(12) United States Patent
Wadsworth et al.

(10) Patent No.: US 8,158,804 B2
(45) Date of Patent: Apr. 17, 2012

(54) CHELATING AGENTS

(75) Inventors: Harry John Wadsworth, Herts (GB);
Ian Martin Newington, Amersham (GB); Clare L. Jones, Harrow (GB); Amanda Ewan, Amersham (GB); Dennis O'Shea, Amersham (GB)

(73) Assignee: GE Healthcare AS, Olso (NO)

( * ) Notice: Subject to any disclaimer, the term of this patent is extended or adjusted under 35 U.S.C. 154(b) by 472 days.

(21) Appl. No.: 12/521,195

(22) PCT Filed: Jan. 11, 2008

(86) PCT No.: PCT/NO2008/000012
§ 371 (c)(1),
(2), (4) Date: Jun. 25, 2009

(87) PCT Pub. No.: WO2008/085064
PCT Pub. Date: Jul. 17, 2008

(65) Prior Publication Data
US 2010/0056787 A1   Mar. 4, 2010

(30) Foreign Application Priority Data

Jan. 11, 2007 (NO) .................................. 20070208
Jun. 4, 2007 (NO) .................................. 20072823

(51) Int. Cl.
*C07D 213/89* (2006.01)
*C07D 213/69* (2006.01)

(52) U.S. Cl. .......................................... 546/296; 546/6
(58) Field of Classification Search ............... 546/6, 296
See application file for complete search history.

(56) References Cited

U.S. PATENT DOCUMENTS

| 2003/0095922 | A1 | 5/2003 | Raymond et al. |
| 2006/0292079 | A1 | 12/2006 | Schmitt-Willich et al. |

FOREIGN PATENT DOCUMENTS

| WO | 94/01406 | 1/1994 |
| WO | 97/00245 | 1/1997 |
| WO | 03/016923 | 2/2003 |
| WO | 2006/069676 | 7/2006 |

OTHER PUBLICATIONS

Hajela, et.al. "A tris-hydroxymethyl-substituted derivative of Gd-TREN-Me-3,2-HOPO: an MRI relaxation agent with improved efficiency" Journal of the American Chemical Society, vol. 122, No. 45, Jan. 1, 2000, pp. 11228-11229.
Caravan, et.al. "Gadolinium(III) chelates as MRI contrast agents: structure, dynamics, and applications" Chemical Reviews, ACS, Washington, D.C., vol. 99, No. 9 Sep. 1, 1999, pp. 2293-2352.
Puerta, et.al. "Tis(pyrone) chelates of Gd(III) as high solubility MRI-CA" Journal of the American Chemcial Society, vol. 128, Jan. 2, 2006, pp. 2222-2223.

*Primary Examiner* — Janet Andres
*Assistant Examiner* — John Mabry

(57) ABSTRACT

The present invention relates to chelating agents, in particular to chelating agents which are capable of forming complexes with paramagnetic metal ions such as iron (III) and gadolinium (III). The invention also relates to the complexes formed and their use as MRI contrast agents.

18 Claims, No Drawings

CHELATING AGENTS

This application is a filing under 35 U.S.C. 371 of international application number PCT/NO2008/000012, filed Jan. 11, 2008, which claims priority to Norwegian application numbers 20070208 filed Jan. 11, 2007 and 20072823 filed Jun. 4, 2007, the entire disclosure of each of which is hereby incorporated by reference.

The present invention relates to chelating agents, in particular to chelating agents that are capable of forming complexes with paramagnetic metal ions such as iron (III) and gadolinium (III). The invention also relates to the complexes formed and their use as MRI contrast agents.

MRI is a medical imaging technique in which areas of the body are visualised via the nuclei of selected atoms, especially hydrogen nuclei. The MRI signal depends upon the environment surrounding the visualised nuclei and their longitudinal and transverse relaxation times, $T_1$ and $T_2$. Thus, in the case when the visualised nucleus is a proton, the MRI signal intensity will depend upon factors such as proton density and the chemical environment of the protons. Contrast agents are often used in MRI in order to improve the imaging contrast. They work by effecting the $T_1$, $T_2$ and/or $T_2^*$ relaxation time and thereby influence the contrast in the images.

Several types of contrast agents have been used in MRI. Blood pool MR contrast agents, for instance superparamagnetic iron oxide particles, are retained within the vasculature for a prolonged time. They have proven to be extremely useful to enhance contrast in the liver but also to detect capillary permeability abnormalities, e.g. "leaky" capillary walls in tumours which are a result of tumour angiogenesis.

Water-soluble paramagnetic metal chelates, i.e. complexes of a chelating agent and a paramagnetic metal ion—for instance gadolinium chelates like Omniscan™ (GE Healthcare)—are widely used MR contrast agents. Because of their low molecular weight they rapidly distribute into the extracellular space (i.e. the blood and the interstitium) when administered into the vasculature. They are also cleared relatively rapidly from the body.

The problem with the in vivo use of paramagnetic metal ions in a MRI contrast agent is their toxicity and therefore they are provided as complexes with chelating agents which are more stable and less toxic.

For a paramagnetic metal chelate to be useful as a contrast agent in MRI, it is necessary for it to have certain properties. Firstly, it must have high stability because it is important that the complex does not break down in situ and release toxic paramagnetic metal ions into the body.

Secondly, in order for it to be a potent MRI contrast agent, a paramagnetic metal chelate must have high relaxivity. The relaxivity of a MRI contrast agent refers to the amount of increase in signal intensity (i.e. decrease in $T_1$) that occurs per mole of metal ions. Relaxivity is dependent upon the water exchange kinetics of the complex.

The solubility of the paramagnetic metal chelate in water is also an important factor when they are used as contrast agents for MRI because they are administered to patients in relatively large doses. A highly water-soluble paramagnetic metal chelate requires a lower injection volume, is thus easier to administer to a patient and causes less discomfort.

U.S. Pat. Nos. 5,624,901 and 5,892,029 both describe a class of chelating agents based on 1-hydroxy-2-pyridinone and 3-hydroxy-2-pyridinone moieties which have a substituted carbamoyl group adjacent the hydroxyl or oxo groups of the ring. The compounds are said to be useful as actinide sequestering agents for in vivo use because of their ability to form complexes with actinides. However, it does not refer directly to the complexes which are formed or to any possibility of using them as MRI contrast agents.

U.S. Pat. No. 4,666,927 also relates to hydroxypyridinones. The preferred compounds have an oxo group in either the 2- or the 4-position and a hydroxyl group in the 1- or 3-position. The only other ring substituents are alkyl groups and the compounds are said to be useful as agents for the treatment of general iron overload.

US-A-2003/0095922 relates to complexes formed between gadolinium (III) ions and an organic ligand. The ligand is said to be based on a pyridinone, pyrimidinone or pyridazinone ring system. The exemplified pyridinone compounds are all 3-hydroxy-2-pyridinones with a carbamoyl group in the 4-position of the ring. The compounds are said to be useful as MRI contrast agents and to have high solubility and low toxicity.

Puerta et al, JACS Chem. Comm. 2006, 128, 2222-2223 describe gadolinium chelates of 3-hydroxy-4-pyrones, which are high relaxivity MRI contrast agents with moderate solubility.

US-A-2006/0292079 describes bifunctional chelates based on the ligands 3-hydroxypyridine-2-one, and 5-hydroxy-pyrimidin-4-one. The gadolinium (III) complexes are used as MRI contrast agents.

The aim of the present invention was to devise new MRI contrast agents which retain the high relaxivity of the compounds described in US 2003/0095922 and by Puerta et al (above) but which have improved solubility, are capable of being easily attached to larger molecules such as peptides, proteins, polymers or dendrimers and have other improved properties. Since the compounds are intended for use as MRI contrast agents, it is also important that they do not polymerise but remain in monomeric form in solution.

Therefore, in a first aspect of the present invention, there is provided a compound of general formula (I):

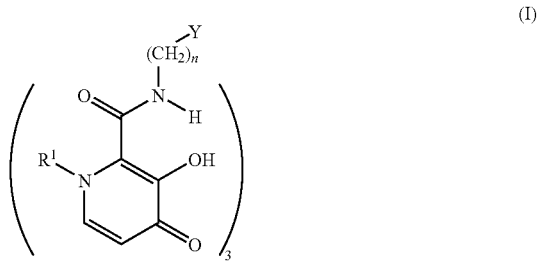

wherein
$R^1$ is $C_{1-6}$ alkyl substituted with OH or O—$C_{1-3}$ alkyl; or polyethylene glycol of up to 3 monomer units.
n is 1-4; and
Y is a trivalent group.

Compounds of general formula (I) are chelating agents that can form complexes with paramagnetic metal ions to obtain paramagnetic metal chelates. These paramagnetic metal chelates have the advantage that they show the high relaxivity of the paramagnetic metal chelates described by Puerta et al. but they have increased solubility in water.

Compounds of general formula (I) may exist in either solvated or unsolvated forms and both are encompassed within the scope of the present invention. The present invention also encompasses all solid forms of the compounds, including amorphous and all crystalline forms.

Certain compounds of general formula (I) may exist in different isomeric forms and the present invention is intended to encompass all isomers including enantiomers, diastereoisomers and geometrical isomers as well as racemates.

In the present specification, the term "$C_{1-6}$ alkyl" refers to a fully saturated straight or branched hydrocarbon chain having from one to six carbon atoms. Examples include methyl, ethyl, n-propyl, isopropyl, n-butyl, isobutyl, t-butyl and n-hexyl.

The group $R^1$ is a moiety which enhances the solubility of the compound of general formula (I). Preferred $R^1$ groups are $C_{2-6}$ alkyl groups substituted with —O—$C_{1-3}$ alkyl groups. It is more preferred that $R^1$ is $C_{2-4}$ alkyl substituted with methoxy or ethoxy. The most preferred $R^1$ group is methoxyethyl.

The trivalent group Y may be any suitable trivalent group, either in form of a single atom or a molecular moiety. Examples are a nitrogen atom, a 1,3,5 trisubstituted phenyl group, a 1,3,5 trisubstituted 2,4,6 trimethylphenyl group, a 1,3,5 cis-trisubstituted cyclohexyl group, a carbon atom substituted with a hydrogen, an amine or a carboxyl group or a carbon atom substituted with a $C_{1-3}$ alkyl substituted with a carboxylate or an amine.

Preferably, therefore, Y is a group of the formula:

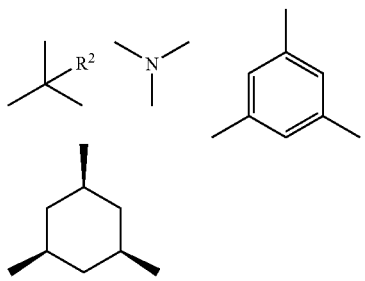

wherein
$R^2$ is H, $(CH_2)_mNH_2$, $(CH_2)_mNHCOPh$, $(CH_2)_mNHCOCH_3$, $(CH_2)_mCO_2H$ or $(CH_2)_mNO_2$; and
m is 0-3
Ph is phenyl If the trivalent group Y contains an amine or a carboxyl group, a paramagnetic metal chelate comprising the compounds of formula (I) as a chelating agent can easily be attached via an amide bond to a larger molecule such as a peptide, protein, polymer or dendrimer. This will give the paramagnetic metal chelate a reduced molecular mobility and therefore increase its relaxivity at high field strengths used in modern MRI scanners. A further advantage of attaching a number of paramagnetic metal chelates to a larger macromolecule is that macromolecules of the correct molecular weight 10-100 k Daltons accumulate in tumours. This allows better detection and delineation of tumours.

In one embodiment the trivalent group Y contains an amine or a carboxyl group and said amine or carboxyl group is reacted with a lipophilic group to result in an amphiphilic compound of formula (I). Suitable lipophilic groups are known in the art and suitable lipophilic groups contain a functional group which reacts with the amine or carboxyl group in said trivalent group Y and a lipophilic residue selected from the group of higher alkyl or higher alkenyl, i.e. containing from about 8-20 carbon atoms, alkylaryl or aralkyl, cholesterol derivatives or bile salts. Suitable lipophilic groups are for instance fatty acid chlorides like oleoyl chloride or stearyl chloride. The amphiphilic compound of formula (I) can then be reacted with for instance a salt containing a paramagnetic metal ion like for instance Gd(III)Cl$_3$ to result in a paramagnetic metal chelate comprising as a chelating agent an amphiphilic compounds of formula (I) (hereinafter denoted "amphiphilic chelate"). The amphiphilic chelate can then be dispersed, optionally in combination with lipids or surfactants or a carrier oil phase to obtain a preferably monodisperse formulation of a chosen size, preferably a micellar size. Techniques for obtaining such a dispersion are known in the art. Alternatively, the amphiphilic compound of formula (I) is dispersed, optionally in combination with lipids or surfactants or a carrier oil phase to obtain a preferably monodisperse formulation of a chosen size, preferably a micellar size and the formulation is then reacted with for instance a salt containing a paramagnetic metal ion like for instance Gd(III)Cl$_3$ to result in a dispersed amphiphilic chelate.

As described earlier, capillary walls in tumours show permeability abnormalities, e.g. "leakiness" which is a result of tumour angiogenesis. By tailoring the size of the dispersed amphiphilic chelates in such a way that the dispersed amphiphilic chelate can pass through these leaky capillary walls into the tumour tissue (e.g. micellar size) it should be possible to obtain an MR imaging agent for tumour imaging.

In another embodiment, other imaging agents may be incorporated into such dispersed amphiphilic chelates, such as X-ray agents or air so that a combined MRI-X-ray or MRI-ultrasound agent would result.

In one embodiment the trivalent group Y contains an amine or a carboxyl group and said amine or carboxyl group is reacted with a functional group which allows the attachment of the compound of formula (I) or a paramagnetic metal chelate comprising the compounds of formula (I) as a chelating agent to a nanoparticle surface. Suitable nanoparticles are metal oxide nanoparticles, gold nanoparticles, silver nanoparticles, silica nanoparticles, zinc nanoparticles or titanium nanoparticles. The choice of functional group depends on the type of nanoparticle the compound of formula (I) is attached to. In a preferred embodiment, the nanoparticle is a gold nanoparticle and the functional group a thiol containing functional group. The thiol group derivatised compound of formula (I) may be attached to the surface of a gold nanoparticle. In another embodiment, the functional group contains a trialkyloxysilane group and such a functional group may be attached to a metal oxide nanoparticle via the trialkyloxysilane group. By attaching paramagnetic metal chelates comprising the compounds of formula (I) as a chelating agent to a nanoparticle, multiple paramagnetic metal chelates are held rigidly relative to one another and this, together with the number of paramagnetic metal chelates per nanoparticle would ensure high relaxivity. In another embodiment, the nanoparticle itself has a function other than just being a carrier. In particular, the nanoparticle may have fluorescent properties thus resulting in a compound which is a combined MR-optical imaging agent.

Other trivalent groups Y are well known to those of skill in the art. Examples of such moieties are shown in for instance US-A-2003/0095922.

As already discussed, the compounds of the present invention may be complexed with paramagnetic metal ions to result in paramagnetic metal chelates that can be used as contrast agents or imaging agents for MRI. Therefore, in a second aspect of the invention there is provided the use of a compound of general formula (I) in the preparation of an MRI contrast agent.

In a further aspect of the invention, there is provided a complex of general formula (II):

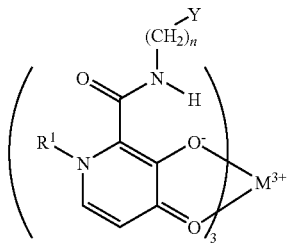

(II)

wherein $R^1$, n, and Y are as defined above for general formula (I) and M is a paramagnetic metal ion.

It is preferred that M is a paramagnetic metal ion of atomic numbers 25, 26, 57 or 60 to 68.

More effective MRI contrast agents are obtained when M is a paramagnetic metal ion of Mn, Fe, La, Eu, Gd or Dy, with Gd being the most preferred.

Preferred $R^1$ and Y groups are as defined above for the first aspect of the invention.

In a further aspect of the invention, there is provided a complex of general formula (II) for use in medicine, particularly as an MRI contrast agent or MR imaging agent. There is also provided the use of a complex of general formula (II) in the preparation of an MRI contrast agent.

Compounds of general formula (II) may be prepared by reacting compounds of general formula (I) with a water soluble salt of a paramagnetic metal ion M, where M is as defined above, in a 1:1 molar ratio. Suitable salts include the nitrate, chloride, acetate and sulphate salts of M and may be in hydrate form.

The reaction is conducted in a suitable solvent such as water, methanol or ethanol or mixtures thereof and in the presence of a base such as pyridine or triethylamine. The resulting product can be purified by reverse phase chromatography or by crystallization.

Compounds of general formula (I) may be prepared by reacting a protected compound of general formula (III)

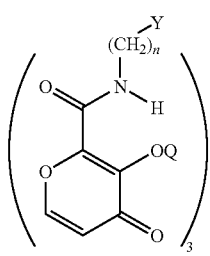

(III)

wherein n, and Y are as defined above for general formula (I) and Q is a protecting group; with a compound of general formula (IV):

$R^1$—$NH_2$ (IV)

wherein $R^1$ is as defined above for general formula (I); to give a protected compound of general formula (V);

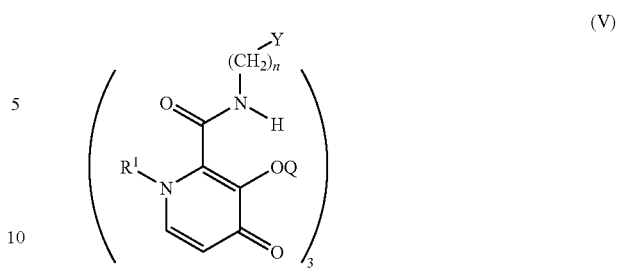

(V)

followed by removal of the protecting group Q.

The reaction is preferably conducted at elevated temperature in a polar solvent such as methanol.

Suitable protecting groups for hydroxyl groups are well known and are described, for example, in "Protecting Groups in Organic Synthesis", Theodora W. Greene and Peter G. M. Wuts, published by John Wiley & Sons Inc. Examples of such groups include tert.-butyl groups or benzyl, with benzyl being the preferred protecting group.

The protecting group can be removed by treatment with either a Lewis acid such as boron trichloride or an acid such as hydrochloric acid in acetic acid.

Compounds of general formula (IV) are well known and are readily available or may be prepared by methods well known to those of skill in the art.

Compounds of general formula (III) may be prepared from 3-benzyloxy-4-oxo-4H-pyran-2-carboxylic acid 2,5-dioxo-pyrrolidin-1-yl ester by reaction with a compound of general formula (VI):

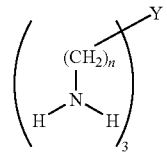

(VI)

wherein Y and n are as defined above for general formula (I).

The reaction is preferably conducted in an organic solvent such as dichloromethane or tetrahydrofuran (THF) under anhydrous conditions.

Some compounds of formula (VI) are known and are readily available or may be prepared by methods well known to those of skilled in the art. Other compounds of formula (VI) may be prepared by methods set out below.

For example, cis-1,3,5 bis aminomethyl cyclohexylmethylamine—a compound of general formula (VI) in which Y is 1,3,5 cyclohexyl and n is 1—can be prepared from cis-1,3,5, cyclohexane tricarboxylic acid by reduction with lithium aluminium hydride followed by reaction of the resulting triol with methyl sulphonyl chloride to give the mesylate, displacement of the methane sulphonyl chloride with azide and hydrogenation following a modification of the method of J. C. Ryu et al., Bull Korean Chem Soc. 2001, Vol. 22 No. 12, 1293-94.

2-[3,5 bis(2-aminoethyl)phenyl]ethylamine—a compound of general formula (VI) in which Y is phenyl and n is 2—was prepared from 1,3,5 tribromomethylbenzene by reacting with sodium cyanide in DMSO and then reducing by hydrogenation with Rayney nickel to give the triamine following the method described by P. Langer et al., Eur J. Org Chem. 2002, 686-691.

4-Nitro-1,7-bis amino-4-{3-aminopropyl}heptane is a compound of general formula (VI) in which Y is C(NO₂) and n is 3 and has the following structure:

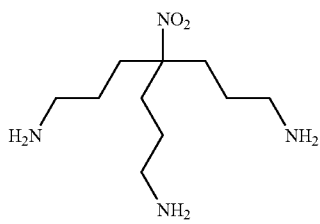

4-Nitro-1,7-bis{N-tert-butoxycarbonylamino}-4-{3-N-[tert-butoxycarbonylamino]propyl}heptane was prepared according to the literature (Bradley et al., Tetrahedron, 2003, 59, 3945-3953). This was then BOC deprotected using TFA to give 4-Nitro-1,7-bis amino-4-{3-aminopropyl}heptane.

The invention will now be described in greater detail by way of the following examples.

EXAMPLE 1

Bis aquo tris(3-hydroxy-1-(2-methoxyethyl)-4-oxo-4-H-pyridin-2yl)carboxyaminoeth-2-yl)-amine lanthanum (III) and Bis aquo tris(3-hydroxy-1-(2-methoxyethyl)-4-oxo-4-H-pyridin-2yl)carboxyaminoeth-2-yl)-amine gadolinium (III), compounds of formula (II)

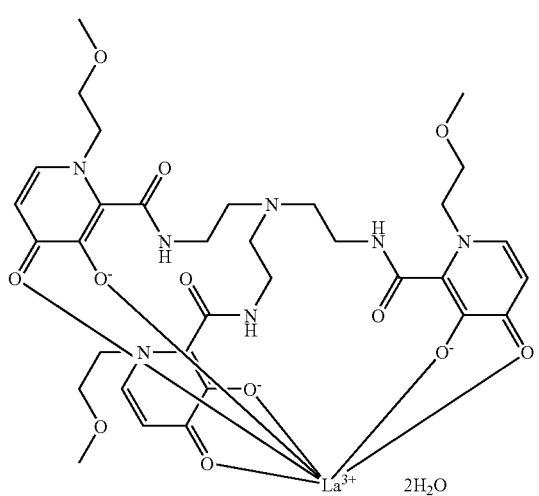

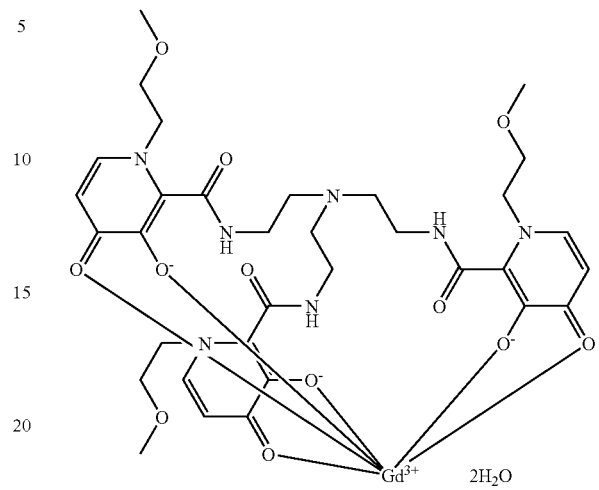

(1a) Tris((3-benzyloxy-4-oxo-4H-pyran-2yl-)carboxyaminoeth-2-yl)-amine

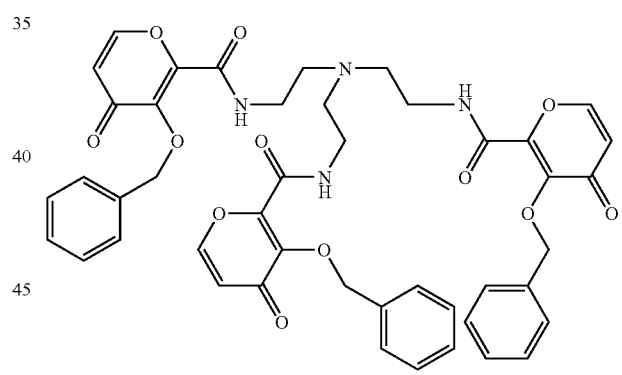

Tris(2-aminoethyl)amine (0.51 ml) and triethylamine (2.9 ml) were added to a solution of 3-benzyloxy-4-oxo-4H-pyran-2-carboxylic acid 2,5-dioxo-pyrrolidin-1-yl ester (3.60 g) (prepared as described in J. Am. Chem. Soc 2006, 128, 2222-2223) in anhydrous THF (40 ml) and stirred at room temperature for 16 hrs. The reaction mixture was concentrated under reduced pressure, the residue partitioned between water and dichloromethane and the organic layer dried (MgSO₄), and concentrated under reduced pressure. The residue was purified by column chromatography on silica, eluting with 0-5% MeOH/CH₂Cl₂ to give the title compound (1.45 g, 51%). 1H NMR (300 MHz, CDCl₃) δ 7.81 (3H, d, J=6 Hz), 7.68 (3H, t, J=6 Hz), 7.35-7.33 (15H, m), 6.46 (3H, d, J=6 Hz), 5.32 (6H, s), 3.12 (6H, t, J=6 Hz), 2.31 (6H, t, J=6 Hz). 13C NMR (300 MHz, CDCl₃) δ 175.66, 158.98, 154.62, 146.98 (2C), 135.42, 129.20, 129.15, 128.85, 117.56, 75.44, 52.05, 37.23. m/z (ES+) 831 (M+H).

(1b) Tris((3-benzyloxy-1-(2-methoxyethyl)-4-oxo-4H-pyridin-2yl-)carboxaminoeth-2-yl) amine

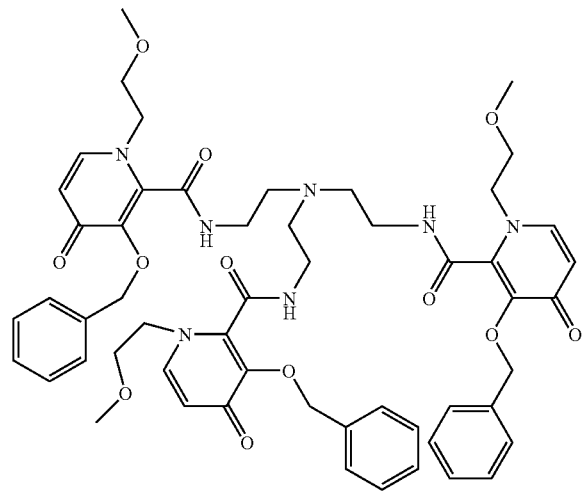

To a solution of tris((3-benzyloxy-4-oxo-4H-pyran-2yl) carboxyaminoeth-2yl-)amine (500 mg) in methanol (10 ml) was added 2-methoxyethylamine (0.42 ml) and the reaction heated to reflux for 3 hrs. The reaction mixture was concentrated under reduced pressure and the residue was purified by column chromatography on silica, eluting with 10% MeOH/$CH_2Cl_2$ to give the title compound (380 mg, 63%). 1H NMR (300 MHz, $CDCl_3$) δ 7.54-7.34 (9H, m), 7.34-7.23 (12H, m), 6.18 (3H, d, J=6 Hz), 5.01 (6H, s), 3.88 (6H, d, J=3 Hz), 3.61 (6H, d, J=3 Hz), 3.30 (9H, s), 2.86 (6H, d, J=6 Hz), 2.15 (6H, d, J=6 Hz). 13C NMR (300 MHz, $CDCl_3$) δ 173.36, 161.01, 144.26, 140.07, 139.35, 136.93, 129.20, 128.44, 128.35, 117.87, 74.59, 71.22, 58.94, 54.12, 52.85, 37.43. m/z (ES+) 1002 (M+H).

(1c) Tris(3-hydroxy-1-(2-methoxyethyl)-4-oxo-4H-pyridin-2yl-)carboxyaminoeth-2-yl) amine

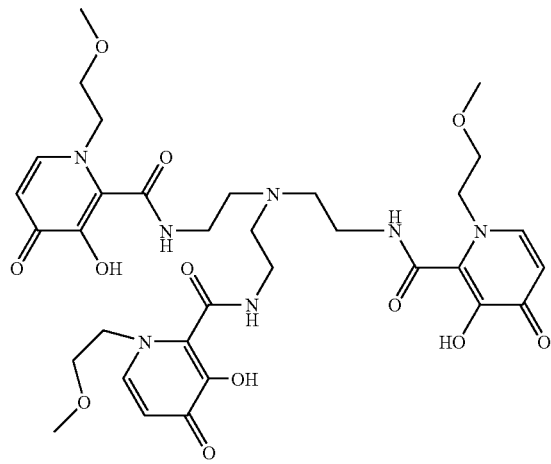

Tris(-3-benzyloxy-1-(2-methoxyethyl)-4-oxo-4H-pyridin-2yl-)carboxyaminoeth-2-yl)amine (300 mg) was stirred in glacial acetic acid (5 ml) and conc. HCl (5 ml) for 3 days. The reaction mixture was concentrated under reduced pressure and used crude in the next step. 1H NMR (300 MHz, DMSO) δ 9.76 (3H, t, J=6 Hz), 8.24 (3H, d, J=6 Hz), 7.51 (3H, d, J=6 Hz), 4.46 (6H, m), 3.82 (6H, m), 3.68 (6H, m), 3.47 (6H, m), 3.22 (9H, s). 13C NMR (300 MHz, DMSO) δ 162.09, 159.85, 143.66, 140.39, 136.67, 112.19, 70.52, 58.84, 56.84, 51.56, 34.71. m/z (ES+) 732 (M+H).

(1d) Bis aquo tris((3-hydroxy-1-(2-methoxyethyl)-4-oxo-1,4-dihydro-pyridine-2yl) carboxyaminoeth-2-yl)amine lanthanum (III) salt

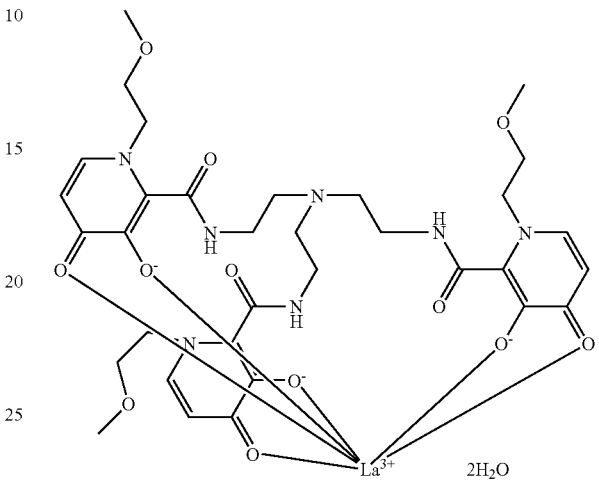

To a solution of tris((3-hydroxy-1-(2-methoxyethyl)-4-oxo-4H-pyridin-2yl-)carboxyaminoeth-2-yl)amine (240 mg) in methanol (20 ml) and water (10 ml) was added lanthanum (III) nitrate hexahydrate (160 mg) and pyridine (2 ml). The reaction was heated to reflux for 2 hrs and then the reaction mixture was concentrated under reduced pressure. The residue was purified by reverse phase chromatography (Gemini column, 5u, C18, 100×30 mm) eluting with 5-95% (0.1% $NH_3$/MeCN)/(0.10% $NH_3$/$H_2O$) to give the title compound (220 mg, 27%). 1H NMR (300 MHz, DMSO) δ 7.43 (3H, d, J=9 Hz), 6.03 (3H, d, J=9 Hz), 4.80 (6H, m), 3.51 (6H, m), 3.11-3.18 (15H, m), 2.42 (6H, d, J=6 Hz). 13C NMR (300 MHz, DMSO) δ 178.46, 164.99, 164.16, 139.55, 119.21, 106.44, 72.04, 58.10, 56.15, 55.82, 36.68. m/z (ES+) 868 (M+H).

(1e) Bis aquo tris(3-hydroxy-1-(2-methoxyethyl)-4-oxo-4H-pyridin-2yl-)carboxyaminoeth-2-yl)amine gadolinium (III) salt

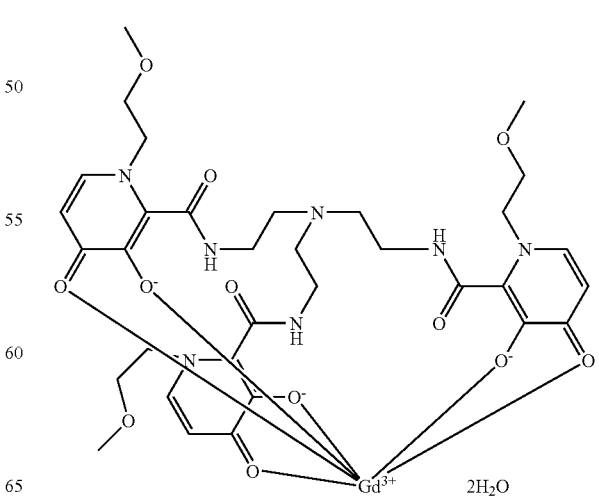

To a solution of tris[2-(carboxyaminoeth-2-yl)-3-hydroxy-1-(2-methoxyethyl)-4-oxo-1,4-dihydro-pyridine]amine (280 mg) in methanol (20 ml) and water (10 ml) was added gadolinium nitrate hexahydrate (212 mg) and pyridine (2 ml). The reaction was heated to reflux for 2 hrs and then the reaction mixture was concentrated under reduced pressure. The residue was purified by reverse phase chromatography (Gemini column, 5u, C18, 100×30 mm) eluting with 5-50% (4% $NH_3$/MeCN)/(4% $NH_3$/$H_2O$) to give the title compound (4 mg, 4%). m/z (ES+) 887 (M+H).

EXAMPLE 2

Tris((3-hydroxy-1-(2-methoxyethyl)-4-oxo-4-H-pyridin-2yl-)carboxyaminoprop-3-yl)-nitro methane gadolinium (III) salt and Tris((3-hydroxy-1-(2-methoxyethyl)-4-oxo-4-H-pyridin-2yl-)carboxyaminoprop-3-yl)-nitro methane lanthanum (III) salt, compounds of formula (II)

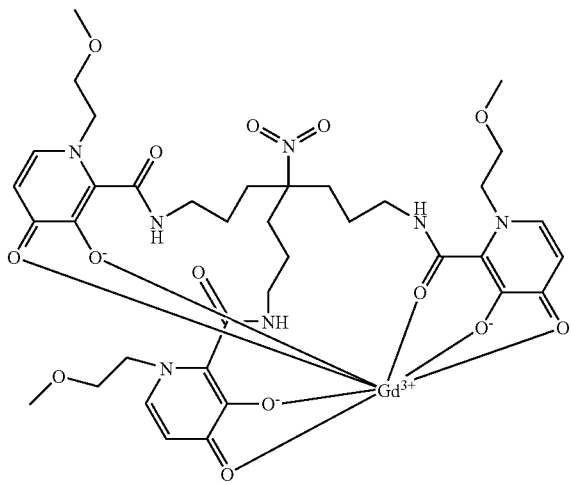

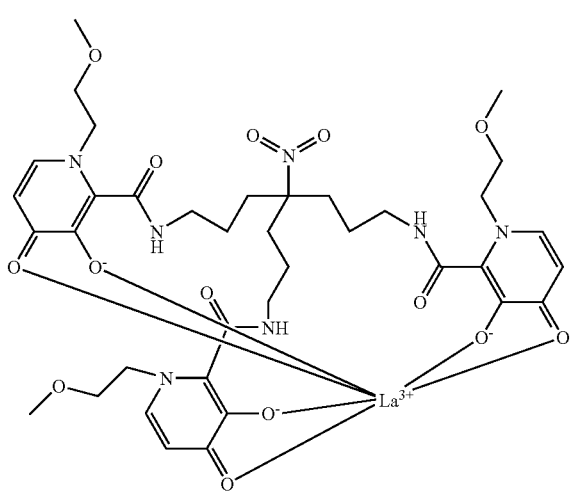

(2a) 4-Nitro-1,7-bis{N-tert-butoxycarbonylamino}-4-{3-N-[tert-butoxycarbonyl amino]propyl}heptane

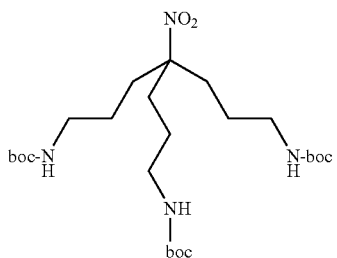

The compound was prepared in two steps from tris-(2-cyanoethyl)nitro methane (1) in 70% yield according to the literature. Bradley et al, Tetrahedron, 2003, 59, 3945-3953
$^1$H-NMR (300 MHz, $CDCl_3$): δ 4.71 (3H, bs, NH); 3.09 (6H, m, 3×$CH_2$—NH); 1.88 (6H, m, 3×$CH_2$—C—NO2); 1.45 (33H, m, 9×$CH_3$+3×$CH_2$).
$^{13}$C NMR (300 MHz, $CDCl_3$): δ 155.97, 93.77, 79.32, 40.12, 32.54, 28.33, 24.20.

(2b) 1,7-diamino-4-Nitro-4-(3-amino-propyl)-heptane trifluoroacetic acid

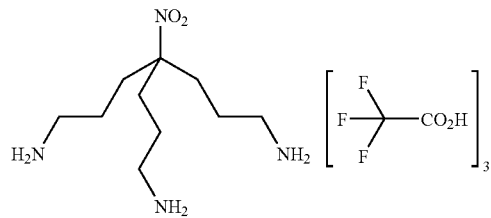

Trifluoroacetic acid (15 ml) was added to a solution of 4-Nitro-1,7-bis{N-tert-butoxycarbonylamino}-4-{3-N-[tert-butoxycarbonylamino]propyl}heptane (2.1 g, 4 mmols) in dry DCM (15 ml). The mixture was stirred at room temperature for 5 hrs. The solvents were removed in vacuo and the residue freeze-dried to give the title compound as a colourless oil (2.3 g, 100%).
$^1$H-NMR (300 MHz, $CD_3OD$): δ 2.97 (6H, m, 3×$CH_2$—NH); 2.07 (6H, m, 3×$CH_2$—C—NO2); 1.66 (6H, m, 3×$CH_2$);
$^{13}$C NMR (75.5 MHz, $CD_3OD$): δ 162.24, 161.73, 161.24, 160.75, 94.16, 40.31, 33.17, 22.91.

(2c) Tris((3-benzyloxy-4-oxo-4H-pyran-2yl)carboxyaminoprop-3-yl)-nitro methane

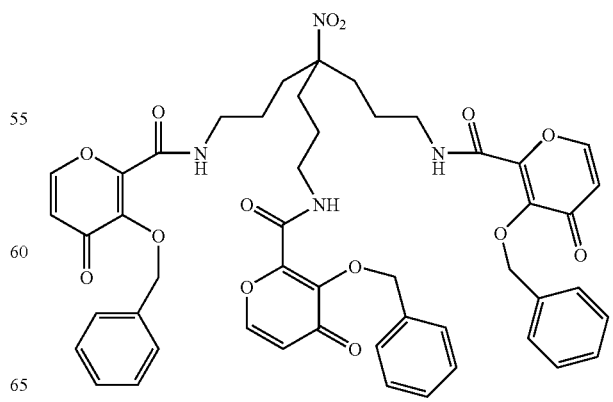

A solution of 3-benzyloxy-4-oxo-4H-pyran-2-carboxylic acid 2,5-dioxo-pyrrolidin-1-yl ester (1.6 g, 4.7 mmol) in anhydrous THF (10 ml) was added to a mixture of 1,7-di-amino-4-Nitro-4-(3-amino-propyl)-heptane trifluoroacetic acid (0.86 g, 1.5 mmol) and triethylamine (1.3 ml, 9.2 mmol) in anhydrous THF (ml) and stirred at room temperature for 24 hrs. The reaction mixture was concentrated under reduced pressure, the residue partitioned between water and dichloromethane and the organic layer dried ($Na_2SO_4$), and concentrated under reduced pressure. The residue was purified by column chromatography on silica, eluting with 3-5% MeOH/$CH_2Cl_2$ to give the title compound as a pale yellow solid (0.57 g, 42%).

$^1$H-NMR (300 MHz, $CDCl_3$): δ 7.81 (3H, d, J=5.9 Hz, CH); 7.74 (3H, bt, NH); 7.36 (15H, s, ArH); 6.47 (3H, d, J=5.9 Hz, CH); 5.39 (6H, s, 3×Ar$CH_2$); 3.14 (6H, m, 3×$CH_2$—NH); 1.67 (6H, m, 3×$CH_2$—C—NO2); 1.14 (6H, m, 3×$CH_2$).

$^{13}$C NMR (300 MHz, $CDCl_3$): δ 177.01, 160.38, 155.92, 148.59, 148.05, 136.67, 130.74, 130, 48, 130.33, 118.93, 94.41, 77.93, 40.60, 33.85, 24.70.

m/z (ES+) 917 (M+H).

(2d) Tris((3-benzyloxy-1-(2-methoxyethyl)-4-oxo-4H-pyridin-2yl-)carboxyamino prop-3-yl)nitromethane

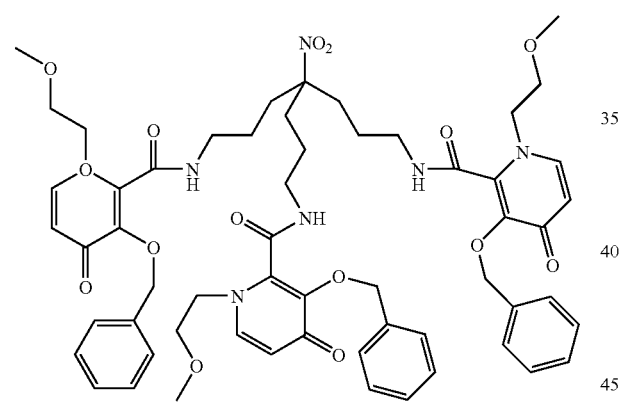

To a solution of tris(3-benzyloxy-4-oxo-4H-pyran-2yl-)carboxyaminoprop-3-yl)nitro-methane (0.55 g, 0.6 mmol) in methanol (15 ml) was added 2-methoxyethylamine (0.41 ml, 4.8 mmol) and the reaction heated to reflux for 1 hr. The reaction mixture was concentrated under reduced pressure and the residue was purified by column chromatography on silica, eluting with 20-50% MeOH/$CH_2Cl_2$ to give the title compound as a yellow solid (370 mg, 57%).

$^1$H-NMR (300 MHz, $CDCl_3$): δ 8.09 (3H, bt, NH); 7.27 (18H, m, ArH+3×CH); 6.08 (3H, d, J=7.4 Hz, CH); 4.93 (6H, s, 3×Ar$CH_2$); 3.90 (6H, m, 3×$CH_2$—N); 3.62 (6H, m, 3×$CH_2$—O); 3.27 (9H, s, OMe); 3.05 (6H, m, 3×$CH_2$—NH); 1.57 (6H, m, 3×$CH_2$—C—NO2); 1.14 (6H, m, 3×$CH_2$).

$^{13}$C NMR (300 MHz, $CDCl_3$): δ 176.47, 163.71, 147.57, 142.77, 142.36, 139.71, 131.06, 131.01, 120.19, 95.52, 79.31, 73.79, 61.59, 56.98, 41.72, 35.16, 25.82 m/z (ES+) 1088 (M+H).

(2e) Tris((3-hydroxy-1-(2-methoxyethyl)-4-oxo-4H-pyridine-2yl-)carboxyaminoprop-3-yl)nitromethane

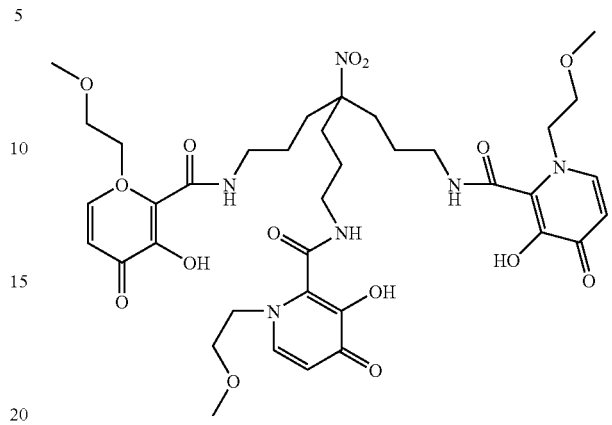

Tris((3-benzyloxy-1-(2-methoxyethyl)-4-oxo-4H-pyridin-2yl)carboxyaminoprop-3-yl)nitro methane (422 mg, 0.4 mmol) was stirred in glacial acetic acid (6 ml) and conc. HCl (6 ml) and heated at 35° C. for 3 days. The reaction mixture was concentrated under reduced pressure to give the title compound as light brown crystals (300 mg, 94%).

$^1$H-NMR (300 MHz, $CD_3OD$): δ 8.16 (3H, d, J=6.8 Hz, CH); 7.17 (3H, d, J=6.8 Hz, CH); 4.51 (6H, m, 3×$CH_2$—N); 3.76 (6H, m, 3×$CH_2$—O); 3.48 (6H, m, 3×$CH_2$—NH); 3.30 (9H, s, OMe); 2.12 (6H, m, 3×$CH_2$—C—NO2); 1.64 (6H, m, 3×$CH_2$).

$^{13}$C NMR (300 MHz, $CD_3OD$): δ 163.49, 161.18, 145.21, 141.27, 137.32, 112.61, 95.27, 71.57, 59.28, 58.13, 40.75, 34.23, 24.52 m/z (ES+) 818 (M+H).

(2f) Tris((3-hydroxy-1-(2-methoxyethyl)-4-oxo-4H-pyridin-2yl-)carboxyaminoprop-3-yl)nitromethane lanthanum (III) salt

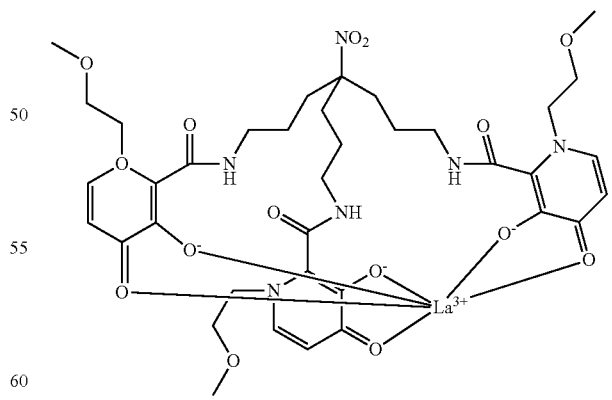

To a solution of tris((3-hydroxy-1-(2-methoxyethyl)-4-oxo-4H-pyridin-2yl-)carboxyaminoprop-3-yl)-nitro methane (50 mg, 0.06 mmol) in methanol (1 ml) and water (1 ml) was added lanthanum (III) nitrate hexahydrate (26 mg, 0.06 mmol) and pyridine (0.15 ml). The reaction was stirred at room temperature for 2 hrs, filtered, washed with methanol (7×5 ml) to give the title compound as a pale pink solid (48 mg, 84%).

$^1$H-NMR (300 MHz, DMSO-d$_6$): δ 10.5 (3H, bs, NH); 7.54 (3H, d, J=6.7 Hz, CH); 6.16 (3H, d, J=6.7 Hz, CH); 4.55 (6H, bs, 3×CH$_2$—N); 3.5 (6H, s, 3×CH$_2$—O); 3.27 (6H, bs, 3×CH$_2$—NH); 3.17 (9H, s, OMe); 1.94 (6H, bs, 3×CH$_2$—C—NO2); 1.38 (6H, bs, 3×CH$_2$).

(2g) Tris((3-hydroxy-1-(2-methoxyethyl)-4-oxo-4H-pyridin-2yl-)carboxyaminoprop-3yl-)nitro methane gadolinium (III) salt

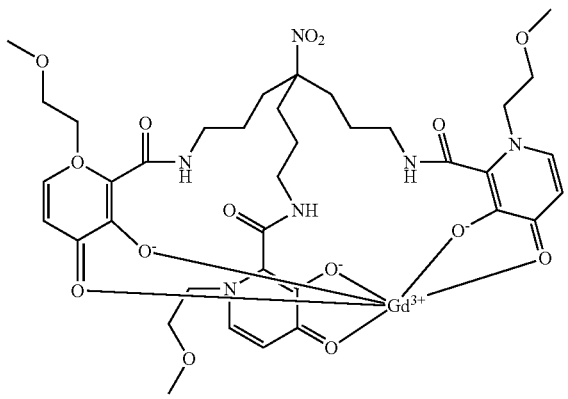

To a solution of tris(3-hydroxy-1-(2-methoxyethyl)-4-oxo-4H-pyridine) carboxyaminoprop-3-yl)nitromethane (50 mg, 0.06 mmol) in methanol (1 ml) and water (1 ml) was added gadolinium (III) nitrate hexahydrate (27 mg, 0.06 mmol) and pyridine (0.15 ml). The reaction was stirred at room temperature for 24 hrs, filtered, washed with methanol (7×5 ml) to give the title compound as a pale brown solid (31 mg, 53%).

EXAMPLE 3

Cis, cis 1,3,5,Tris((3-hydroxy-1-(2-methoxyethyl)-4-oxo-4H-pyridine-2yl-)carboxy aminomethyl)cyclohexane Lanthanum (III) salt, compound of formula (II)

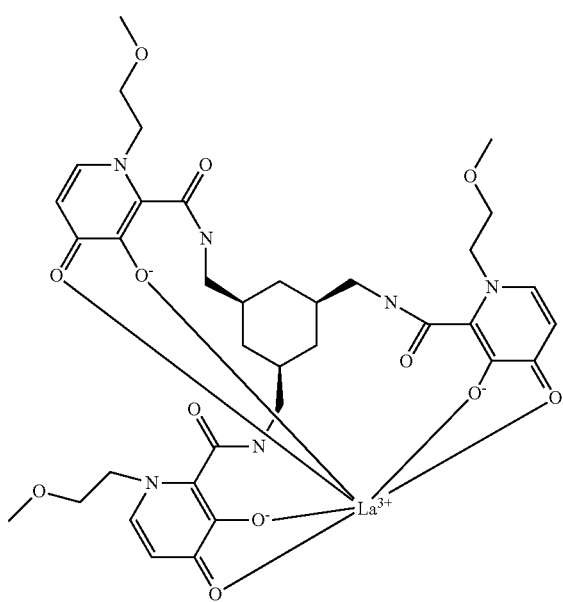

(3a) Cis,cis,tris 1,3,5-acetoxymethylcyclohexane

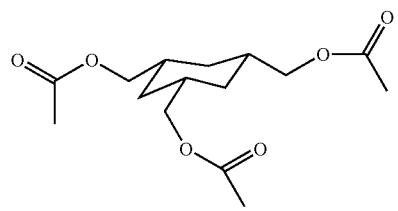

Lithium aluminium hydride (4.4 g) in THF (100 ml) was stirred and treated cautiously with trimethyl cis cis-1,3,5-cyclohexane tricarboxylate (10g) in THF (50 ml) over the period of ca. 1 hr. A strongly exothermic reaction occurred causing the solvent to reflux strongly. The reaction was heated under gentle reflux for 3 days. The reaction had cooled and stirred and acetic acid (19 ml) was added drop wise and stirring continued until hydrogen evolution ceased. Acetic anhydride (95 ml) was added, the flask was equipped for distillation and heated to 90° C. with stirring when the THF distilled out. A further portion of acetic anhydride (95 ml) was added. The reaction was then heated at 140° C. for 5 hrs during which time the reaction changed from a thick grey paste to a very fine powder. The reaction was filtered and the solid washed with ethyl acetate. The filtrate was evaporated and dried in high vacuum to afford cis cis tris 1,3,5-acetoxymethylcyclohexane (11.7 g, 100%) as a yellow liquid in quantitative yield. This material was used directly in the next step.

$^1$H NMR (300 MHz; CDCl$_3$) δ, 0.68-0.79 (3H, m, CH×3), 1.8-1.89 (6H, m, CH×6), 2.06 (9H, s, Me×3), 3.92 (6H, J$_{HH}$ 6 Hz, CH$_2$×3).

$^{13}$C NMR (75 MHz; CDCl$_3$), δ 21.0 (Me×3), 32.4 (CH×3), 36.1 (CH×3), 69.0 (OCH$_2$×3), 171.2 (C=O).

(3b) Cis, cis,tris (1,3,5-hydroxymethyl)cyclohexane

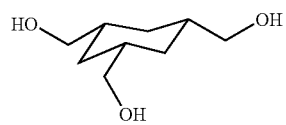

Cis, cis 1,3,5-tris (acetoxymethyl)cyclohexane (11.7 g) in 1N hydrochloric acid (80 ml) and ethanol (80 ml) was heated under reflux and stirred overnight. The solvent was then removed under reduced pressure and the gum dried in high vacuum to give cis, cis 1,3,5-tris hydroxymethyl cyclohexane (6.7 g).

$^1$H NMR (300 MHz; CD$_3$OD), δ 0.56 (3H, q, J$_{HH}$ 12 Hz, CH×3), 1.56 (3H, m, CH×3), 1.87 (3H, m, CH×3), 3.34 (6H, d, J$_{HH}$ 6 Hz, OCH$_2$).

$^{13}$C NMR (75 MHz; CD$_3$OD), δ 32.6 (CH$_2$), 39.5 (C), 67.3 (OCH$_2$).

(3c) Cis, cis, tris 1,3,5-(methanesulphonyloxymethyl)cyclohexane

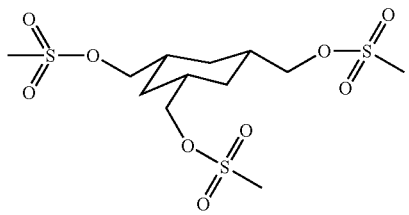

Cis, cis, tris 1,3,5 (hydroxy methyl)cyclohexane (9.6 g) in anhydrous dichloromethane was slowly treated with pyridine (45 ml) and methane sulphonyl chloride (14 ml) at room temperature. The reaction was stirred at room temperature for 18 hrs. After which time the solvent was removed from the reaction mixture in vacuo. The residue was then washed with water. The organics were then extracted with dichloromethane, dried over MgSO$_4$, filtered and evaporated to dryness to give the crude title compound (12.5 g, 57%).

$^1$H NMR (300 MHz; CDCl$_3$), δ 0.78-0.95 (3H, m, CH×3), 1.82-1.98 (6H, m, CH$_2$×3), 3.03 (9H, s, Me×3), 4.09 (6H, d, J$_{HH}$ 6 Hz, OCH$_2$×3).

$^{13}$C NMR (75 MHz; CDCl$_3$), δ 31.2 (Me), 36.3 (CH$_2$×3), 37.5 (CH×3), 73.5 (OCH$_2$).

(3d) Cis, cis-1,3,5-tris azidomethyl cyclohexane

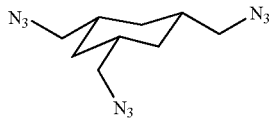

Cis, cis, 1,3,5-tris (methanesulphonyloxymethyl)cyclohexane (12 g, 29 mmole) in dry DMF (150 ml) was treated with sodium azide (13.4 g, 206 mmole added portion wise) under nitrogen over five minutes with stirring. The mixture was heated at 50° C. overnight. Upon cooling the reaction was treated with dilute potassium carbonate solution (300 ml) and extracted three times with petrol ether 40/60: diethyl ether 50:50. The organic extracts were washed with water and dried over sodium sulphate. The combined aqueous layers were carefully poured into a large container charged with excess bleach solution and ice. The internal temperature of this was kept below 25° C. (to ensure that the release of nitrogen was controlled). The organic layer was diluted with ethanol 100 ml and the solution concentrated in vacuo to (50 ml) to remove most of the petrol ether. A small sample was evaporated to dryness $^1$H/$^{13}$C then run:

$^1$H NMR (300 MHz; CDCl$_3$), δ0.65-0.81 (3H, m, CH×3), 1.60-1.95 (6H, m, CH×6), 3.21 (6H, d, J$_{HH}$ 6 Hz, NCH$_2$×3).

$^{13}$C NMR (75 MHz; CDCl$_3$), 33.2 (CH$_2$×3), 36.0 (CH$_2$×3), 57.3 (CH$_2$N).

(3e) Cis, cis 1,3,5-trisaminomethyl cyclohexane

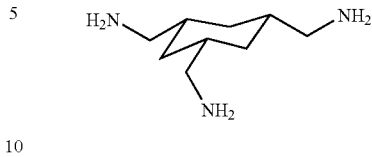

1,3,5-tris azidomethyl cyclohexane (7.5 g) and 600 mg 10% palladium on carbon in ethanol (50 ml) was shaken with hydrogen for 3 hrs. (The N$_2$ produced as removed and replaced by more H$_2$). The reaction mixture was then filtered through a pad of celite and evaporated to dryness to give 5.5 g of cis cis,1,3,5,tris aminomethyl-cyclohexane $^{13}$C NMR δ (75 MHz; CDCl$_3$), 34.8 (CH×3), 40.3 (CH$_2$×3), 48.7 (CH$_2$N).

(3f) Cis, cis 1,3,5,tris((3-benzyloxy-4-oxo-4H-pyran-2yl)carboxyaminomethyl)cyclohexane

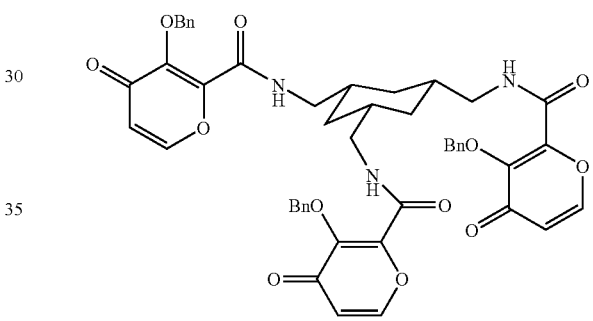

3-Benzyloxy-4-oxo-4H-pyran-2-carboxylic acid 2,5-dioxo-pyrrolidin-1-yl ester (6.6 g 19.3 mmol) prepared as described in J. Am. Chem. Soc 2006 128, 2222-2223.) was added to cis, cis 1,3,5-tris aminomethyl-cyclohexane (1 g, 5.3 mmole) and triethylamine (2 g 19.8 mmole) in tetrahydrofuran (250 ml). The reaction mixture was stirred overnight at room temperature. TLC (10% methanol in dichloromethane on silica) indicated that the starting material had been consumed. The solvent was removed in vacuo. The residue was then washed with water and the organics extracted with dichloromethane. The organic phase was then dried over MgSO$_4$, filtered and evaporated to dryness to afford the crude material as a yellow oil. This was then purified by flash chromatography (DCM 99%, MeOH 1%-DCM 10% over 17CV) to afford cis, cis 1,3,5,tris(3-benzyloxy-4-oxo-4H-pyran-2yl)carboxyaminomethyl)cyclohexane as a yellow foam (0.62 g, 12%).

$^1$H (CDCl$_3$; 300 MHz), δ 0.29 (3H, q, J$_{HH}$ 12 Hz, CH×3), 1.13-1.30 (3H, m, CH×3), 1.34-1.44 (3H, m, CH×3), 2.97 (6H, t, J$_{HH}$ 6 Hz, NCH$_2$×3), 5.39 (6H, s, OCH$_2$), 6.51 (3H, d, J$_{HH}$ 6 Hz, CH×3), 7.36 (18H, s, ArCH×15, CH×3) 7.55 (3H, brs NH×3). $^{13}$C (CDCl$_3$; 75 MHz), δ 34.3 (CH×3), 36.5 (CH$_2$×3), 45.5 (NCH$_2$×3), 117.7 (CH×3), 129.1 (ArCH×15), 129.4 (ArCH×3), 135.4 (ArC×3), 147.1 (C—O×3), 147.2 (C—O), 154.7 (CH—O×3), 159.1 (C=O), 175.8 (C=O).

(3g) Cis, cis 1,3,5,tris(3-benzyloxy-1-(2-methoxy-ethyl)-4-oxo-4H-pyridine-2-yl-)carboxyaminomethyl)-cyclohexane

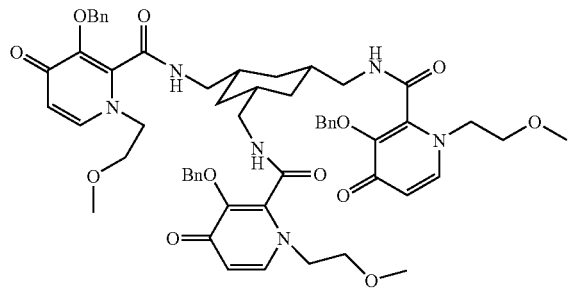

Cis, cis 1,3,5,tris(3-benzyloxy-4-oxo-4H-pyran-2-carboxyaminomethyl)cyclohexane (0.52 g, 0.61 mmole) in methanol (75 ml) was treated with 2-methoxyethyl amine (0.41 ml, 4.79 mmole) and heated under reflux for 1 hr. TLC (DCM/MeOH 90:10 on silica) indicated that the starting materials had been consumed. The solvents were then removed under reduced pressure and the residue was purified by flash chromatography in a gradient of 10% to 30% methanol in dichloromethane. Cis, cis 1,3,5,tris((3-benzyloxy-1-(2-methoxyethyl)-4-oxo-4H-pyridin-2yl-)carboxyaminomethyl)cyclohexane was obtained as a yellow foam (335 mg, 52%).

$^1$H NMR (300 MHz; CDCl$_3$), δ 0.39 (3H, q, J$_{HH}$ 12 Hz, CH×3), 1.17-1.39 (3H, m, CH×3), 1.66-1.80 (3H, m, CH×3), 2.94 (6H, br s, NCH$_2$×3), 3.26 (9H, s, OMe×3), 3.57 (6H, t, J$_{HH}$ 5 Hz, NCH$_2$×3), 3.95 (6H, br s, OCH$_2$×3), 5.06 (6H, s, OCH$_2$×3), 6.10 (3H, d, J$_{HH}$ 7 Hz, CH×3), 7.20-7.40 (18H, m, ArCH×15, NCH×3), 8.01 (3H, br s, NH×3).

$^{13}$C NMR (75 MHz; CDCl$_3$), δ 34.6 (CH×3), 36.7 (CH$_2$×3), 45.6 (NCH$_2$×3), 54.3 (NCH$_2$×3), 59.0 (OMe), 71.3 (OCH$_2$×3), 72.0 (OCH$_2$×3), 117.5 (CH×3), 128.0 (ArCH×3), 128.4 (ArCH×2), 137.4 (ArC×3), 139.8 (C—N×3), 140.2 (C—N×3), 145.2 (C—O), δ 161.1 (C=O), 174.0 (C=O).

(3h) Cis, cis 1,3,5,tris((3-hydroxy-1-(2-methoxyethyl)-4-oxo-4H-pyrid-2yl-)carboxyaminomethyl)-cyclohexane

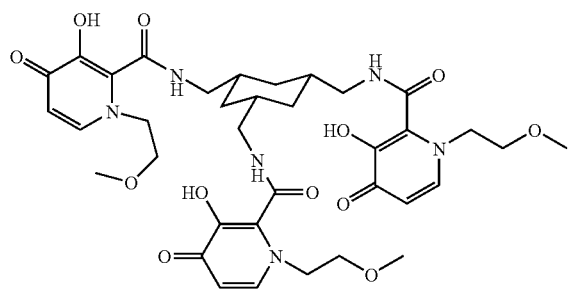

Cis, cis 1,3,5,tris((-3-benzyloxy-1-(2-methoxyethyl)-4-oxo-4H-pyridine-2yl-)carboxyaminomethyl)cyclohexane (300 mg) was stirred in glacial acetic acid (5 ml) and conc. HCl (5 ml) for 2 days at 37° C. The reaction mixture was concentrated under reduced pressure and used crude in the next step. The solution had turned bright yellow in colour. The solvent was removed in vacuo. Methanol (3×15 ml) was added and was then removed in vacuo to afford a yellow solid (220 mg).

$^1$H NMR (300 MHz; CDCl$_3$) δ, 0.73 (6H, q, J$_{HH}$ 15 Hz, CH×3), 1.50-1.68 (3H, m, CH×3), 1.83-1.90 (3H, m, CH×3), 3.16-3.35 (15H, m/s, CH$_2$×3, OMe), 3.67 (6H, t, J$_{HH}$ 5 Hz, NCH$_2$×3), 4.36 (6H, br s, OCH$_2$×3), 7.16 (3H, d, J$_{HH}$ 7 Hz, CH×3), 8.06 (3H, d, J$_{HH}$ 7 Hz, CH×3).

$^{13}$C NMR (75 MHz; CDCl$_3$) δ, 34.1 (CH×3), 36.6 (CH×3), 45.2 (NCH$_2$×3), 55.8 (NCH$_2$×3), 58.3 (OMe), 70.0 (OCH$_2$×3), 111.4 (CH×3), 136.5 (C—N×3), 139.5 (C—N×3), 143.1 (C—O×3), 162.1 (C=O×3), 172.0 (C=O).

(3i) cis, cis 1,3,5,tris(2-carboxyaminomethyl-3-hydroxy-1-(2-methoxyethyl)-4-oxo-1,4-dihydro pyridine) cyclohexane lanthanum (III) salt

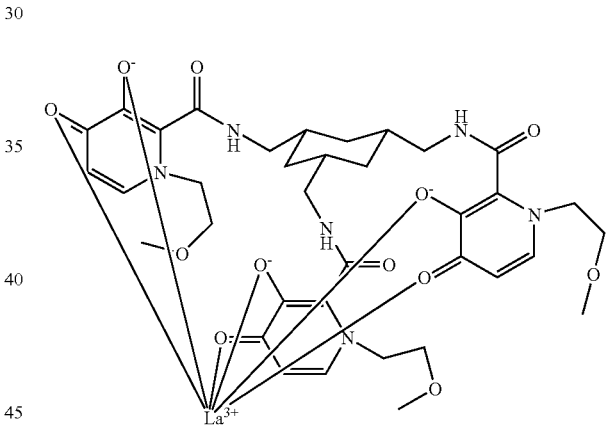

To a solution of cis, cis 1,3,5,tris(2-carboxyaminomethyl-3-hydroxy-1-(2-methoxyethyl)-4-oxo-1,4-dihydro pyridine) cyclohexane (60 mg) in methanol (10 ml) and water (10 ml) was added lanthanum nitrate hexahydrate (30 mg) and pyridine (1 ml). The reaction was heated to reflux for 2 hrs and then the reaction mixture was concentrated under reduced pressure. The residue was washed with methanol to give Lanthanum (III) cis, cis 1,3,5,tris(2-carboxyaminomethyl-3-hydroxy-1-(2-methoxyethyl)-4-oxo-1,4-dihydropyridine) cyclohexane as a pale pink solid (40 mg 68%).

$^1$H NMR (300 MHz; CDCl$_3$) δ, 0.70 (6H, q, J$_{HH}$ 15 Hz, CH×3), 1.52 (3H, m, CH×3), 1.8-2.0 (3H, m, CH×3), 3.18 (9H, s, OMe×3), 3.4-3.7 (12H, NCH$_2$×3, OCH$_2$×3), 4.7 (6H, br m, OCH$_2$×3), 6.14 (3H, d, J$_{HH}$ 7 Hz, CH×3), 7.53 (3H, d, J$_{HH}$ 7 Hz, CH×3).

EXAMPLE 4

Bis aquo tris(-3-hydroxy-1-(2-hydroxyethyl)-4-oxo-4H-pyridin-2yl-)2-(carboxyaminoeth-2-yl)-amine gadolinium (III) salt, compound of formula (II)

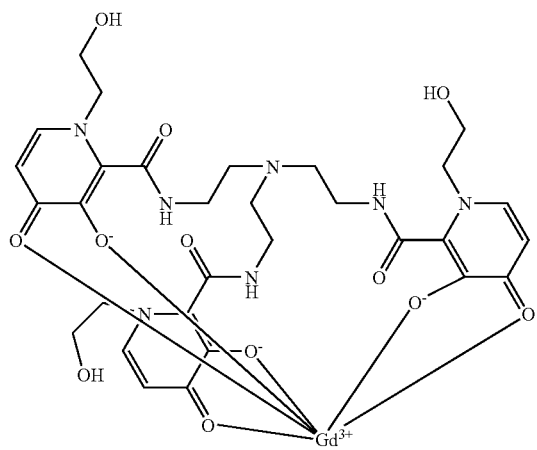

(4a) Tris((3-benzyloxy-1-(2-hydroxyethyl)-4-oxo-4H-pyridin-2yl-)carboxaminoeth-2-yl)amine

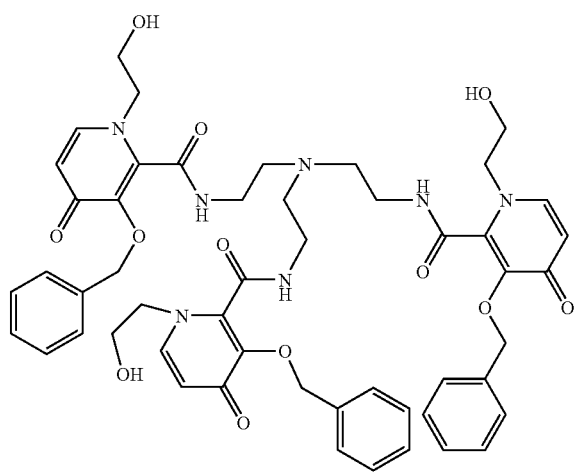

Tris(3-benzyloxy-1-(2-hydroxyethyl)-4-oxo-4H-pyridin-2yl)carboxaminoeth-2-yl)-amine (4a) was synthesized using the procedure for (1b) except that the ethanolamine was used instead of 2-methoxyethylamine. The product was purified by column chromatography on silica, eluting with 0-40% methanol/dichloromethane to give the title compound (4b) as a yellow foam (1.5 g, 52%).

$^1$H NMR (300 MHz, DMSO) δ 8.79 (3H, t, J=6 Hz), 7.60 (3H, d, J=6 Hz), 7.41-7.27 (15H, m), 6.24 (3H, d, J=6 Hz), 5.06 (6H, s), 3.87 (6H, d, J=6 Hz), 3.66 (6H, d, J=6 Hz), 3.20 (6H, d, J=6 Hz), 2.46 (2H, d, J=6 Hz),

13C NMR (300 MHz, DMSO) δ 173.32, 161.39, 144.76, 140.98, 139.83, 138.19, 128.73, 128.52, 128.33, 117.14, 73.33, 60.78, 56.21, 53.09, 39.81.

m/z (ES+) 959 (M−H).

(4b) Tris[-3-hydroxy-1-(2-hydroxyethyl)-4-oxo-4H-pyridin-2yl-]2-(carboxyaminoeth-2-yl)-amine

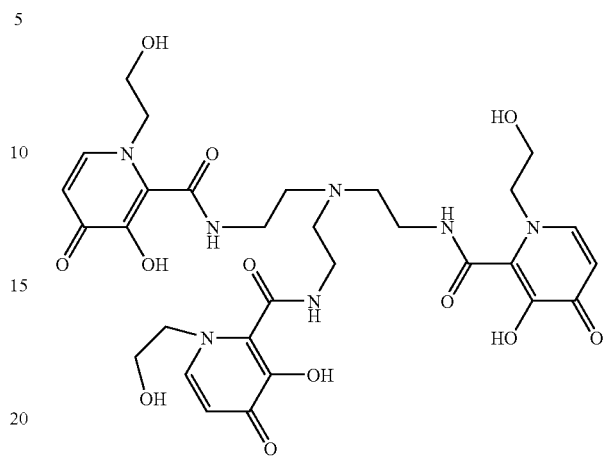

Tris(3-benzyloxy-1-(2-hydroxyethyl)-4-oxo-1,4-dihydro-pyridin-2yl-)carboxaminoeth-2-yl)-amine (4a) (1.5 g) was hydrogenated with 10% Pd/C (100 mg) in methanol (100 ml) at 10 psi at room temperature for 4 days. The reaction was filtered through Hyflo and the filtrate concentrated in vacuo and dried under vacuum to give the title compound (4b) as an orange solid (430 mg, 30%).

1H NMR (300 MHz, MeOD) δ 7.50 (3H, d, J=9 Hz), 6.21 (3H, d, J=6 Hz), 4.17 (6H, bs), 3.84 (6H, bs), 3.57 (6H, bs), 2.82 (6H, bs).

13C NMR (300 MHz, MeOD) δ 169.61, 162.02, 146.94, 138.92, 128.85, 110.95, 60.91, 57.67, 52.76, 37.50.

LC/MS (Gemini 150×4.6 mm, 3-20% acetonitrile in water over 12 minutes) showed the material at 4.76 min m/z (ES+) 690 (M+H).

Elemental analysis: % calculated C, 52.25; H, 5.70; N, 14.21. % found C, 48.72; H, 5.40; N, 13.08.

(4) Bis aquo tris(-3-hydroxy-1-(2-hydroxyethyl)-4-oxo-4H-pyridin-2yl-)carboxyaminoeth-2-yl)-amine gadolinium (III) salt

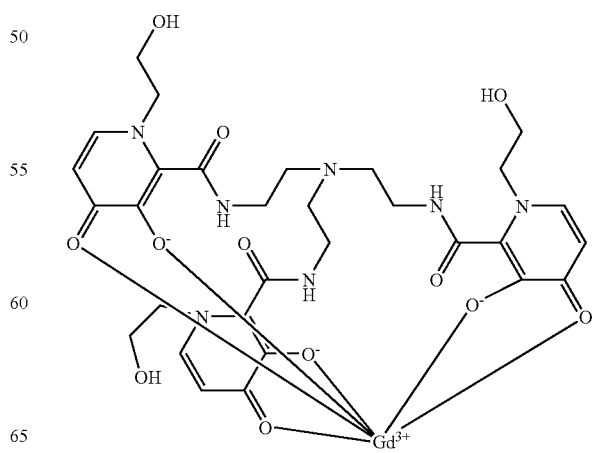

To a solution of tris[-3-hydroxy-1-(2-hydroxyethyl)-4-oxo-1,4-dihydro-pyridin-2yl-]2-(carboxyaminoeth-2-yl)-amine (4b) (470 mg) in methanol (5 ml) and water (5 ml) was added gadolinium (III) acetate (204 mg). The reaction was heated to reflux for 2 hrs, cooled and the precipitate filtered off and dried under vacuum to give the title compound (4) as an orange solid (400 mg, 74%).

LC/MS (Gemini 150×4.6 mm, 3-20% acetonitrile in water over 12 minutes) showed the material at 6.61 min m/z (ES+) 845 (M+H).

Elemental analysis: % calculated C, 42.70; H, 4.30; N, 11.61; Gd, 18.63. % found C, 39.86; H, 4.20; N, 10.58; Gd; 16.73.

EXAMPLE 5

Bis aquo tris(3-hydroxy-1-(2-(2-hydroxyethoxy)ethyl)-4-oxo-4H-pyridin-2yl-)carboxyaminoeth-2-yl)amine gadolinium (III) salt, compound of formula (II)

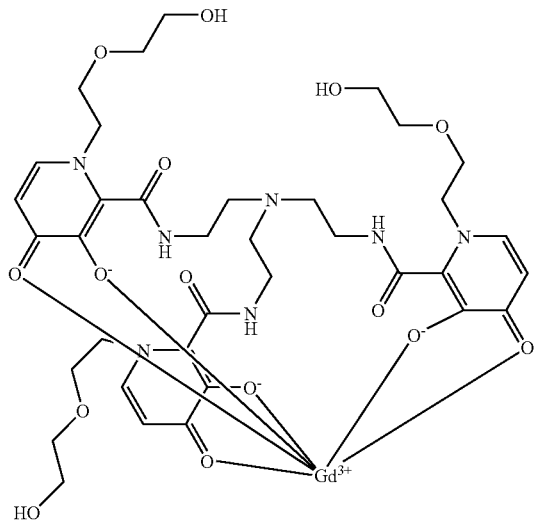

(5a) Tris(3-benzyloxy-1-(2(2-hydroxyethoxy)ethyl)-4-oxo-4H-pyridin-2yl-)carboxaminoeth-2-yl)amine

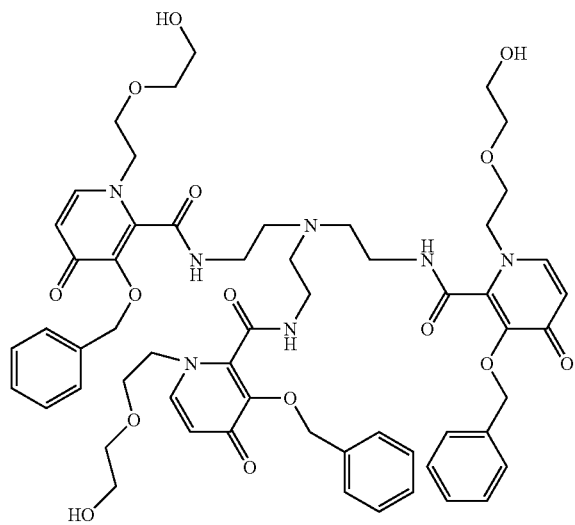

Tris((3-benzyloxy-1-(2(2-hydroxyethoxy)ethyl)-4-oxo-4H-pyridin-2yl-)1-carboxaminoeth-2-yl)amine was synthesized using the procedure for (1b) except that 2(2-hydroxyethyl)ethylamine was used instead of 2-methoxy-ethylamine. The product was purified by column chromatography on reverse phase silica, eluting with 10-60% methanol/water to give the title compound (4c) as a yellow crystalline solid (682 mg, 52%).

1H NMR (300 MHz, MeOD) δ 7.73 (3H, d, J=9 Hz), 7.20-7.50 (15H, m), 6.47 (3H, d, J=9 Hz), 5.08 (6H, s), 4.07 (6H, t, J=6 Hz), 3.72 (6H, d, J=6 Hz), 3.59 (6H, m), 3.45 (6H, m), 3.20 (6H, t, J=6 Hz), 2.42 (6H, t, J=6 Hz).

13C NMR (300 MHz, MeOD) δ 174.51, 161.61, 144.93, 140.80×2, 137.22, 128.40, 128.18, 128.03, 117.12, 74.22, 72.41, 69.43, 60.76, 52.82, 37.58.

LC/MS (Gemini 150×4.6 mm, 5-95% acetonitrile in water over 6 minutes) showed the material at 3.24 min m/z (ES+) 1092 (M+H).

(5b) Tris((3-hydroxy-1-(2-(2-hydroxyethoxy)ethyl)-4-oxo-4H-pyridin-2yl-)carboxyaminoeth-2-yl)aine

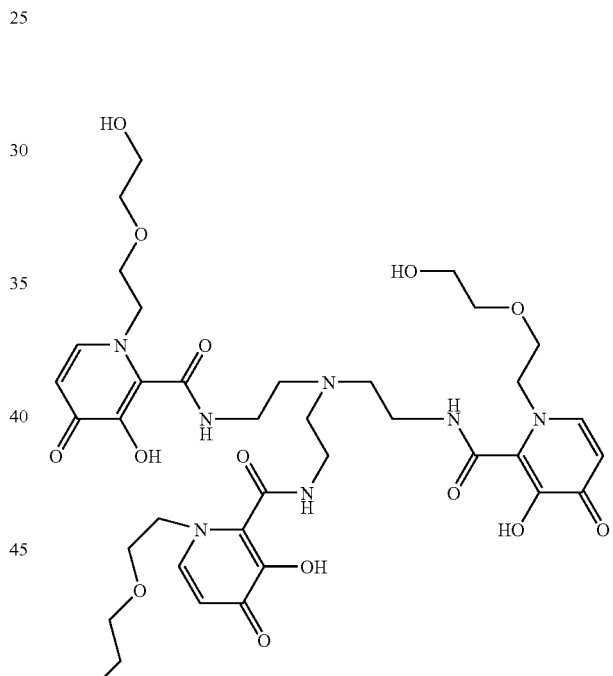

(5b) Tris(3-hydroxy-1-(2-(2-hydroxyethoxy)ethyl)-4-oxo-1,4-dihydro-pyridin-2yl-)carboxyaminoeth-2-yl)amine was synthesized from Tris(3-benzyloxy-1-(2(2-hydroxyethoxy)ethyl)-4-oxo-1,4-dihydro-pyridin-2yl-)1-carboxaminoeth-2-yl)amine (5a) using the procedure to prepare (4b) to give the title compound as an orange foam (480 mg, 98%).

1H NMR (300 MHz, MeOD) δ 7.57 (3H, d, J=9 Hz), 6.28 (3H, d, J=9 Hz), 4.22 (6H, t, J=6 Hz), 3.74 (6H, t, J=6 Hz), 3.61-3.45 (18H, m), 2.82 (6H, t, J=6 Hz).

13C NMR (300 MHz, MeOD) δ 170.60, 162.10, 147.00, 139.35, 128.26, 110.90, 72.36, 69.81, 60.78, 54.97, 53.29, 37.81.

LC/MS (Gemini 150×4.6 mm, 5-95% acetonitrile in water over 6 minutes) showed the material at 1.95 min m/z (ES+) 822 (M+H).

(5) Bis aquo tris((3-hydroxy-1-(2-(2-hydroxyethoxy) ethyl)-4-oxo-4H-pyridin-2yl-)carboxyaminoeth-2-yl) amine gadolinium (III) salt

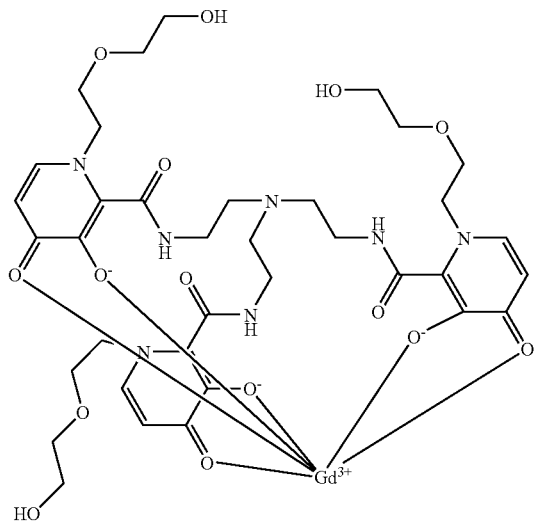

(5) was synthesized from Tris(3-hydroxy-1-(2-(2-hydroxyethoxy)ethyl)-4-oxo-1,4-dihydro-pyridin-2yl-)carboxyaminoeth-2-yl)amine (5b) using the same procedure as for (4) to give the title compound (5) (138 mg, 59%).

LC/MS (Gemini 150×4.6 mm, 5-95% acetonitrile in water over 6 minutes) showed the material at 2.09 min m/z (ES+) 977 (M+H).

Elemental analysis: % calculated C, 44.30; H, 4.96; N, 10.04. % found C, 42.50; H, 4.81; N, 9.61.

EXAMPLE 6

Bis aquo tris((3-hydroxy-1-(2,3-dihydroxypropane)-4-oxo-4H-pyrid-2yl-)carboxyaminoeth-2-yl)-amine gadolinium (III) salt, compound of formula (II)

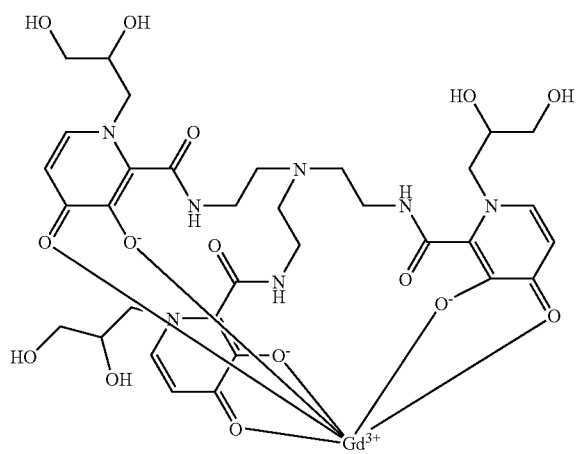

(6a) Tris-((3-benzyloxy-1-(propane-2,3-diol)-4-oxo-4H-pyridin-2yl-) carboxaminoeth-2-yl)amine

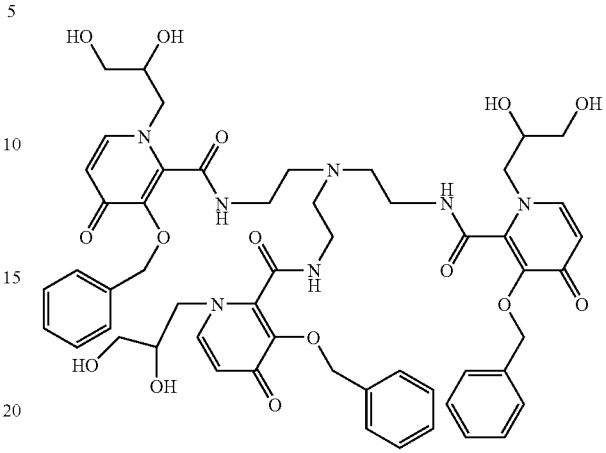

(6a) was synthesized using the procedure for (4b) except that 2,3-dihydroxyaminopropane was used instead of 2-methoxyethanolamine. The product was purified by column chromatography on reverse phase silica, eluting with 50% methanol/water to give the title compound (6a) (465 mg, 41%).

1H NMR (300 MHz, MeOD) δ 7.72 (3H, d, J=9 Hz), 7.20-7.50 (15H, m), 6.42 (3H, d, J=9 Hz), 5.20-4.90 (6H, m), 4.30-3.40 (15H, m), 3.20-2.90 (6H, m), 2.40-2.10 (6H, m).

13C NMR (300 MHz, MeOD) δ 175.35, 162.51, 14.71, 142.77, 142.40, 137.70, 130.62, 129.81, 129.62, 118.57, 76.35, 72.14, 64.78, 59.02, 38.30.

LC/MS (Gemini 150×4.6 mm, 5-95% acetonitrile in water over 6 minutes) showed the material at 2.96 min m/z (ES+) 1050 (M+H).

(6b) Tris((3-hydroxy-1-(2,3-dihydroxypropane)-4-oxo-4H-pyridin-2yl)carboxyaminoeth-2-yl)-amine

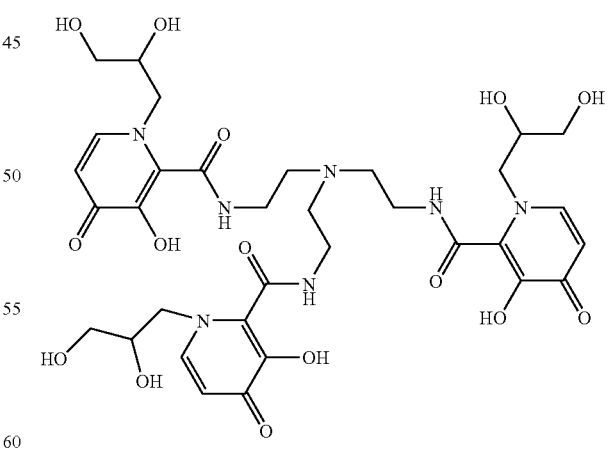

(6b) was synthesized from Tris-((3-benzyloxy-1-(propane-2,3-diol)-4-oxo-1,4-dihydro-pyridin-2yl-)carboxaminoeth-2-yl)amine (6a) using the procedure for (4b) to give the title compound as a cream foam (220 mg, 56%).

1H NMR (300 MHz, MeOD) δ 7.39 (3H, t, J=6 Hz), 6.09 (3H, d, J=6 Hz), 4.60-3.40 (21H, m), 2.82 (6H, t, J=6 Hz).

13C NMR (300 MHz, MeOD) δ 172.15, 171.90, 163.82, 140.33, 140.18, 129.88, 112.24, 111.94 72.46, 72.38, 69.37, 65.16, 64.89, 59.92, 59.83, 54.46, 54.28, 43.63, 38.98

(6) Bis aquo tris((3-hydroxy-1-(2,3-dihydroxypropane)-4-oxo-4H-pyrid-2yl-)carboxyaminoeth-2-yl)-amine gadolinium (III) salt

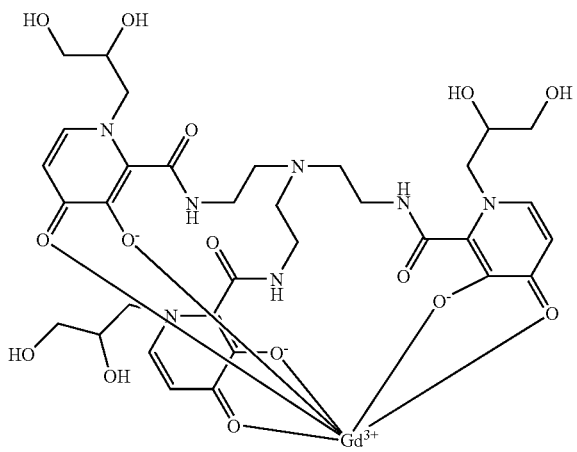

(6) was synthesized from (6b) Tris(3-hydroxy-1-(2,3-dihydroxypropane)-4-oxo-4H-pyridin-2yl)carboxyaminoeth-2-yl)-amine using the procedure for (4) to give the title compound (6) (140 mg, 63%).

LC/MS (Gemini 150×4.6 mm, 5-95% acetonitrile in water over 6 minutes) showed the material at 1.68 min m/z (ES+) 933 (M+H).

Elemental analysis: % calculated C, 42.44; H, 4.53; N, 10.49; Gd, 16.84. % found C, 40.19; H, 4.95; N, 9.64; Gd, 15.12.

EXAMPLE 7

Bis aquo tris(3-hydroxy-1-(2,3,4-trihydroxybutane)-4-oxo-4H-pyridin-2yl-)carboxyaminoeth-2-yl)amine gadolinium (III) salt, compound of formula (II)

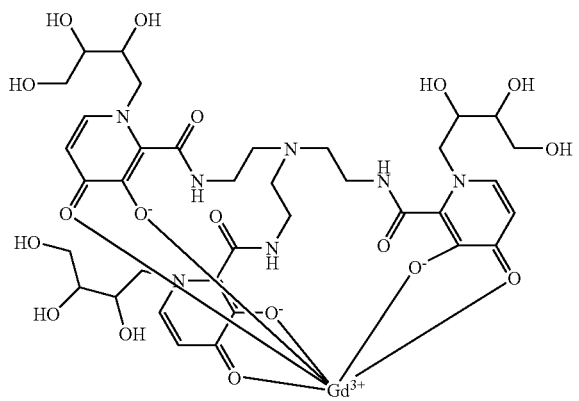

(7a) Tris((3-benzyloxy-1-(2,3,4-trihydroxybutane)-4-oxo-4H-pyridin-2yl-)carboxaminoeth-2-yl)amine

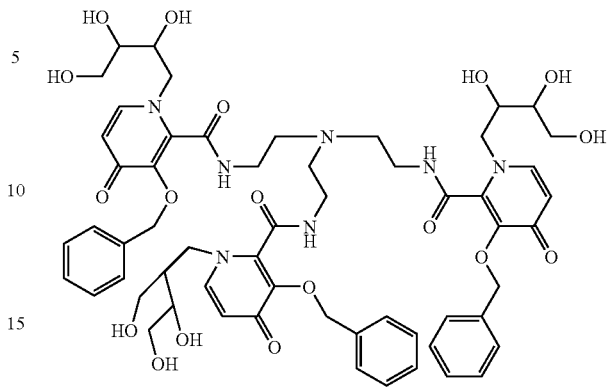

(7a) was synthesized using the same procedure as for (4b) except that 4-amino-1,2,3-butanetriol (Myriam Petta, EP 0 675 105 A1, page 10) was used instead of 2-methoxyethylmine. The product was purified by column chromatography on reverse phase silica, eluting with 10-50% methanol/water to give the title compound (7a) (481 mg, 35%).

1H NMR (300 MHz, MeOD) δ 7.72 (1H, d, J=6 Hz), 7.20-7.50 (5H, m), 6.42 (1H, d, J=6 Hz), 5.20-4.90 (2H, m), 4.30-3.90 (3H, m), 3.70-3.50 (3H, m), 3.30-2.80 (2H, m), 2.40-2.10 (2H, m).

13C NMR (300 MHz, MeOD) δ 175.27, 162.51, 145.62, 142.55, 142.46, 137.65, 130.57, 129.80, 129.60, 118.61, 76.35, 73.50, 71.77, 63.96, 73.50, 71.77, 63.96, 58.95, 53.08, 38.37.

LC/MS (Gemini 150×4.6 mm, 5-95% acetonitrile in water over 6 minutes) showed the material at 2.85 min m/z (ES+) 1140 (M+H).

(7b) Tris((3-hydroxy-1-(2,3,4-trihydroxybutane)-4-oxo-4H-pyrid-2yl-) carboxyaminoeth-2-yl)amine

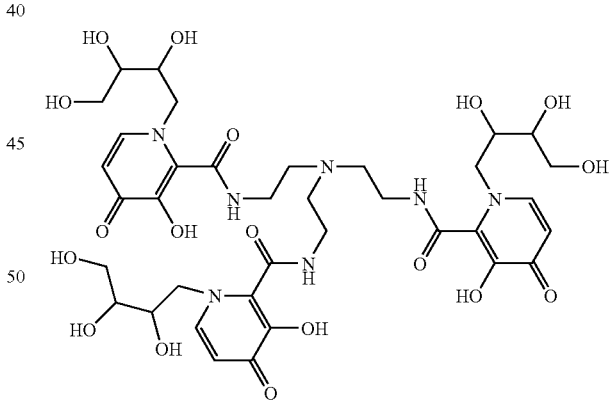

(7b) was synthesized from (7a) using the procedure for (4b) but with water added to the reaction mixture to give the title compound as an orange solid (268 mg, 77%).

1H NMR (300 MHz, DMSO) δ 7.39-7.20 (3H, m), 6.02-5.80 (3H, m), 4.60-3.40 (21H, m), 4.30-4.10 (3H, m), 3.90-3.70 (6H, m), 3.50-3.10 (15H, m), 2.80-2.50 (6H, m).

13C NMR (300 MHz, DMSO) δ 172, 162, 139, 127, 110, 72, 70, 62, 67, 53, 48.

LC/MS (Gemini 150×4.6 mm, 5-95% acetonitrile in water over 6 minutes) showed the material at 1.19 min m/z (ES+) 870 (M+H).

(7) Bis aquo tris((3-hydroxy-1-(2,3,4-trihydroxybu-
tane)-4-oxo-4H-pyridin-2yl-)carboxyaminoeth-2-yl)
amine gadolinium (III) salt

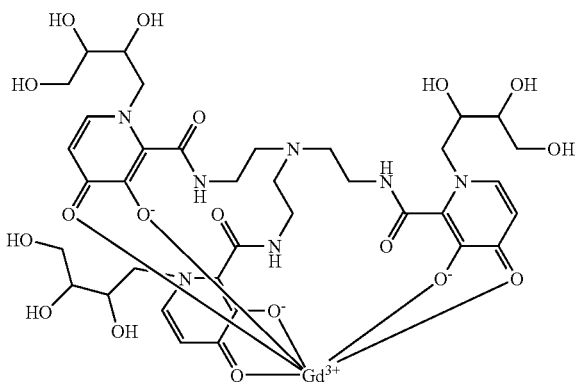

(7) was synthesized from (7b) using the procedure for (4) to give Bis aquo tris((3-hydroxy-1-(2,3,4-trihydroxybutane)-4-oxo-4H-pyridin-2yl-)carboxyaminoeth-2-yl)amine gadolinium (III) salt (7) (127 mg, 100%).

LC/MS (Gemini 150×4.6 mm, 5-95% acetonitrile in water over 6 minutes) showed the material at 1.43 min m/z (ES+) 1025 (M+H).

EXAMPLE 8

Bis aquo tris((3-oxy-1-(2,3,4,5,6-pentahydroxyhex-
ane)-4-oxo-4H-pyridin-2yl-)carboxyaminoeth-2-yl)
amine gadolinium (III) salt, compound of formula
(II)

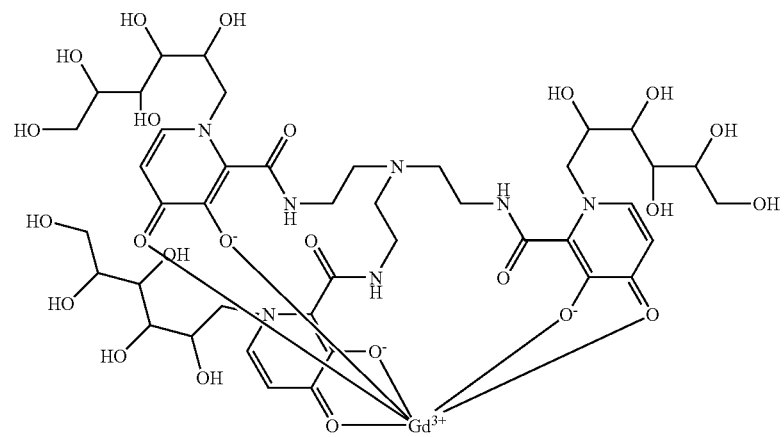

(8a) Tris((3-benzyloxy-1-(2,3,4,5,6-pentahydroxy-
hexane)-4-oxo-4H-pyridin-2yl-)carboxaminoeth-2-
yl)amine

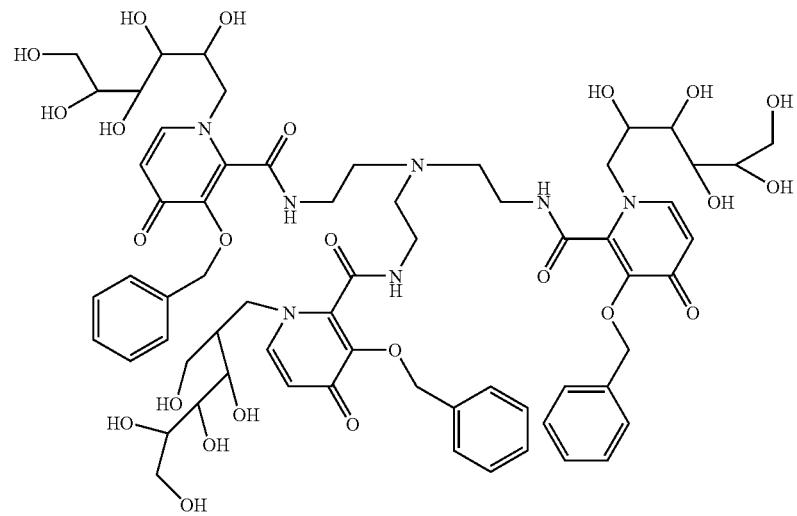

(8a) was synthesized using the procedure for (4b) except that using D-glucamine instead of methoxyethylamine. The product was purified by column chromatography on reverse phase silica, eluting with 30-50% methanol/water to give the title compound (8a) (900 mg, 57%).

1H NMR (300 MHz, DMSO) δ 8.62 (3H, m), 7.56 (3H, d, J=9 Hz), 7.40-7.20 (15H, m), 6.22 (3H, d, J=9 Hz), 5.30-5.20 (3H, m), 5.10-4.90 (6H, m), 4.80-4.30 (12H, m), 4.10-3.0 (12H, m), 2.50-2.30 (6H, m).

13C NMR (300 MHz, DMSO) δ 172.67, 160.71, 144.02, 141, 139.59, 137.41, 128.17, 128.12, 127.84, 72.90, 72.36, 71.29, 71.19, 69.50, 63.24, 56, 52, 37.

LC/MS (Gemini 150×4.6 mm, 5-95% acetonitrile in water over 6 minutes) showed the material at 2.69 min m/z (ES+) 1320 (M+H) and (ES+) 661 (M+2/2).

(8b) Tris((3-hydroxy-1-(2,3,4,5,pentahydroxyhexane)-4-oxo-4H-pyridin-2yl-)carboxyaminoeth-2-yl)-amine

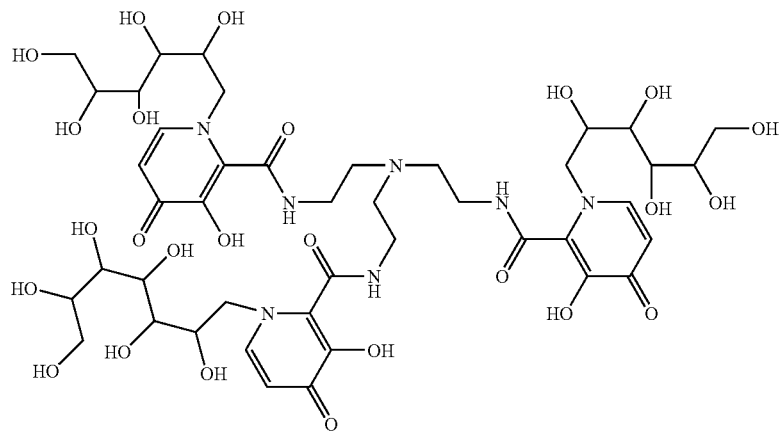

(8b) was synthesized from (8a) using the procedure for (4b) to give Tris((3-hydroxy-1-(2,3,4,5,pentahydroxyhexane)-4-oxo-4H-pyridin-2yl-)carboxyaminoeth-2-yl)-amine (8b) as an orange solid (393 mg, 94%).

1H NMR (300 MHz, DMSO) δ 7.42 (3H, d, J=6 Hz), 6.07 (3H, d, J=6 Hz), 4.30-2.50 (36H, m). 13C NMR (300 MHz, DMSO) δ 170.66, 161.47, 139.16, 127.49, 110.34, 72.43, 71.57, 71.35, 71.25, 69.55, 63.26, 57.17, 52.95, 38.

LC/MS (Gemini 150×4.6 mm, 5-95% acetonitrile in water over 6 minutes) showed the material at 0.63 min m/z (ES+) 1050 (M+H) and (ES+) 525 (M+2/2).

(8) Bis aquo tris((3-hydroxy-1-(2,3,4,5,6-pentahydroxyhexane)-4-oxo-4H-pyridin-2yl-]carboxyaminoeth-2-yl)amine gadolinium (III)

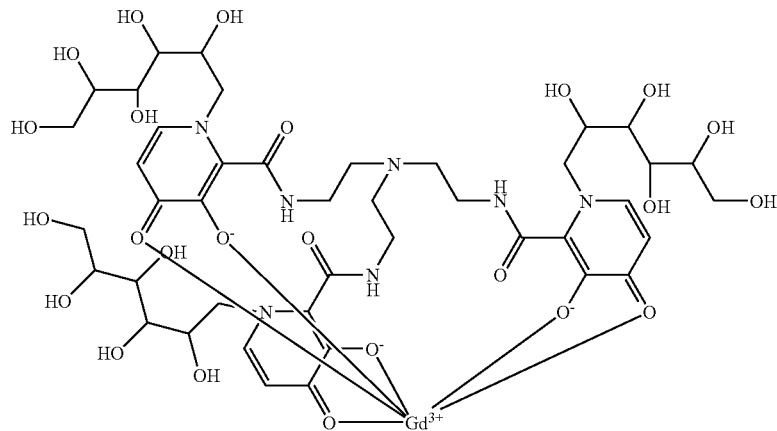

(8) was synthesized using the procedure for (4) using (8b) to give aquo tris((3-hydroxy-1-(2,3,4,5,6-pentahydroxyhexane)-4-oxo-1,4-dihydro-pyridin-2yl-]carboxyaminoeth-2-yl)amine gadolinium (III) salt (8).

LC/MS (Gemini 150×4.6 mm, 5-95% acetonitrile in water over 6 minutes) showed the material at 0.76 min m/z (ES+) 603 (M+2/2) and (ES+) 302 (M+4/4).

Elemental analysis: % calculated C, 41.89; H, 5.02; N, 8.14; Gd, 13.09. % found C, 39.34; H, 5.37; N, 7.25; Gd, 9.30.

EXAMPLE 9

Tris((3-hydroxy-1-(2-hydroxyethyl)-4-oxo-4H-pyridin-2-yl)-carboxyaminoprop-3-yl)-]nitromethane, compound of formula (I)

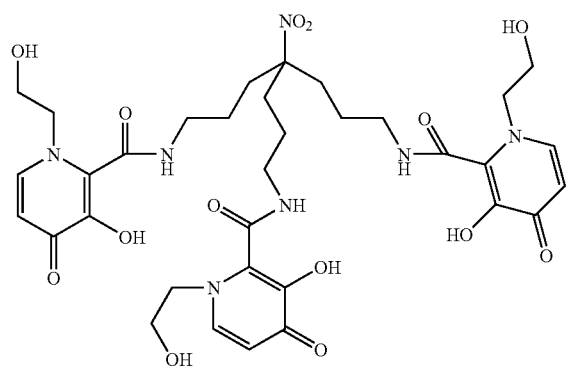

(9a) Tris((3-benzyloxy-1-(2-hydroxyethyl)-4-oxo-4H-pyridin-2-yl)=carboxyaminoprop-3-yl)nitromethane

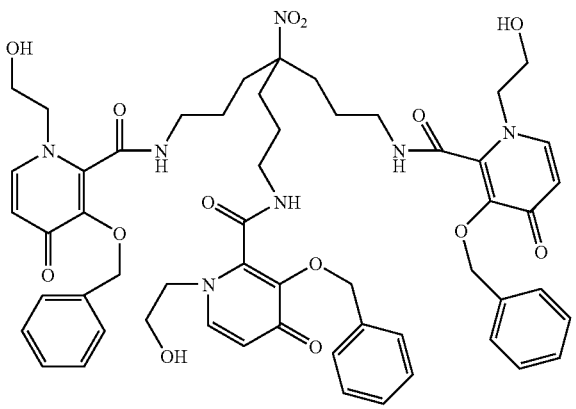

A mixture of (2c) Tris((3-benzyloxy-4-oxo-4H-pyran)carboxyaminoprop-3-yl)nitro methane (0.50 g, 0.55 mmol), 2-ethanolamine (0.27 g, 4.4 mmol) in anhydrous methanol (10 ml) under nitrogen was heated to reflux for 1 hr. The reaction mixture was concentrated in vacuo and the residue purified by column chromatography on silica, eluting with 30-70% MeOH/DCM to afford the title compound (9a) (260 mg, 45%) as a yellow solid. The sample was azeotroped with methanol/toluene to remove final traces of 2-ethanolamine.

$^1$H NMR (300 MHz, CD$_3$OD) δ 1.19 (m, 6H), 1.66 (m, 6H), 3.14 (m, 6H), 3.83 (m, 6H), 4.00 (m, 6H), 5.06 (s, 6H), 6.45 (d, J=7.7 Hz, 3H), 7.35 (m, 15H), 7.71 (d, J=7.7 Hz, 3H).

$^{13}$C NMR (75 MHz, CD$_3$OD) δ24.4, 33.8, 40.5, 57.9, 61.9, 75.6, 94.7, 118.5, 129.4, 129.6, 129.7, 138.3, 142.0, 142.2, 146.3, 162.8, 175.7 m/z (ES$^-$) 1044.4 (M$^-$H).

(9) Tris((3-hydroxy-1-(2-hydroxyethyl)-4-oxo-4H-pyridin-2-yl)-carboxyaminoprop-3-yl)nitromethane

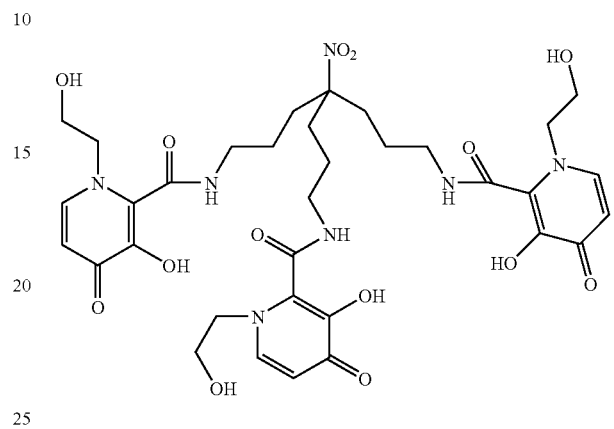

To a solution of (9a) (0.10 g, 0.1 mmol) in methanol (15 ml) was added palladium 10% wt on activated carbon (0.10 g). The mixture was hydrogenated at 2 bar at room temperature for 3 hrs. The reaction mixture was filtered through glass fibre filter paper, the paper washed with water (10 ml), methanol from the filtrate removed in vacuo and freezed-dried to afford the title compound (34 mg, 44%) as a dark orange solid.

Note: all glassware and reaction vessels were soaked with 5 N HCl, washed with distilled water and dried in an oven to remove any potential iron contamination.

$^1$H NMR (300 MHz, D$_2$O) δ 1.57 (m, 6H), 2.07 (m, 6H), 3.41 (m, 6H), 3.79 (m, 6H), 4.15 (m, 6H), 6.45 (bs, 3H), 7.60 (bs, 3H).

$^{13}$C NMR (75 MHz, D$_2$O) δ 22.8, 32.6, 39.5, 57.2, 60.7, 94.9, 112.7, 129.1, 139.7, 147.5, 163.1, 171.9 m/z (ES$^+$) 776.3 (M+H).

EXAMPLE 10

Tris((3-hydroxy-1-(2-hydroxyethyl)-4-oxo-4H-pyridin-2-yl)-carboxyaminoprop-3-yl)aminomethane, compound of formula (I)

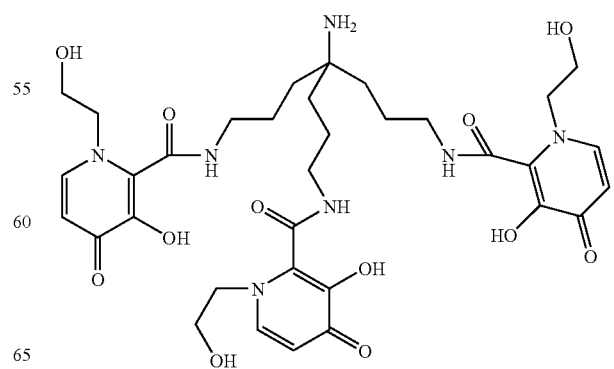

(10a) Tris((3-benzyloxy-1-(2-hydroxyethyl)-4-oxo-4H-pyridin-2-yl)-carboxyaminoprop-3-yl)-]aminomethane

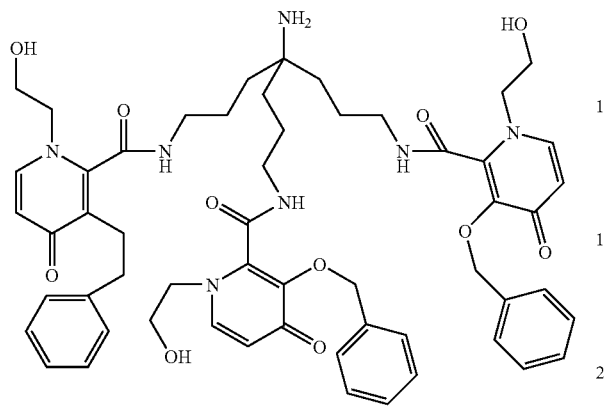

A mixture of (9a) (0.11 g, 0.11 mmol) and Raney-Nickel (1.4 g) in ethanol (20 ml) was hydrogenated at 2 bar at 40° C. for 24 hrs. The reaction mixture was filtered through glass fibre filter paper and solvents removed in vacuo to afford the title compound (10a) (70 mg, 63%) as an orange solid.

$^1$H NMR (300 MHz, CD$_3$OD) δ 1.17 (m, 6H), 1.28 (m, 6H), 3.20 (m, 6H), 3.83 (m, 6H), 4.03 (m, 6H), 5.10 (s, 6H), 6.50 (bs, 3H), 7.20-7.50 (m, 15H), 7.74 (bs, 3H).

$^{13}$C NMR (75 MHz, CD$_3$OD) δ24.0, 37.5, 41.3, 54.2, 57.9, 61.9, 75.4, 118.5, 129.3, 129.5, 138.6, 142.1, 142.2, 146.6, 162.8, 176.0, 180.2 m/z (ES$^+$) 1016.5 (M$^+$H).

(10) Tris((3-hydroxy-1-(2-hydroxyethyl)-4-oxo-4H-pyridin-2-yl)-carboxyaminoprop-3-yl)-]aminomethane

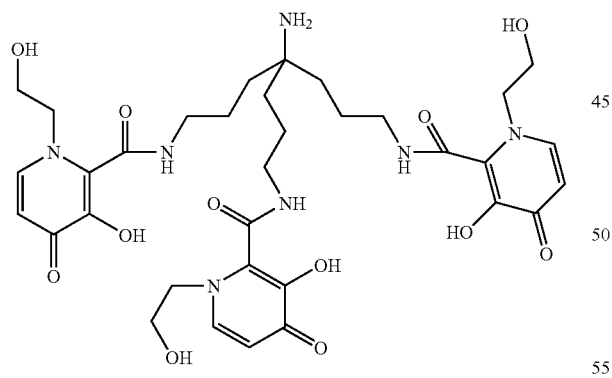

To a solution of Tris((3-benzyloxy-1-(2-hydroxyethyl)-4-oxo-4H-pyridinone-2-yl)-carboxyaminopropyl)aminomethane (10a) (70 mg, 0.07 mmol) in methanol (15 ml) was added palladium 10% wt on activated carbon (100 mg). The mixture was hydrogenated at 2 bar at room temperature for 24 hrs. The reaction mixture was filtered twice through glass fibre filter paper and solvents removed in vacuo to afford the title compound (10) (43 mg, 82%) as an orange solid.

$^1$H NMR (300 MHz, D$_2$O) δ 1.50-2.00 (m, 12H), 3.40 (m, 6H), 3.76 (m, 6H), 4.20 (m, 6H), 6.34 (bs, 3H), 7.43 (bs, 3H).

m/z (ES$^+$) 746.3 (M$^+$H).

EXAMPLE 11

Tris((3-hydroxy-1-(2-methoxyethyl)-4-oxo-4H-pyridin-2-yl)-carboxyaminoprop-3-yl)phenylcarboxyaminomethane, compound of formula (I)

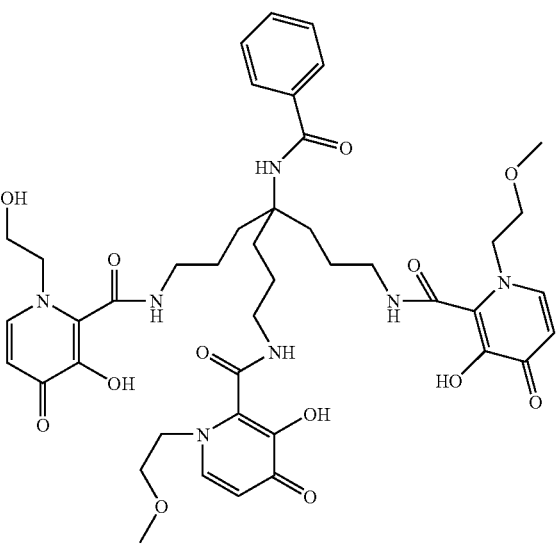

(11a)
Tris(3-tertbutoxycarboxyaminoprop-3yl-)amino methane

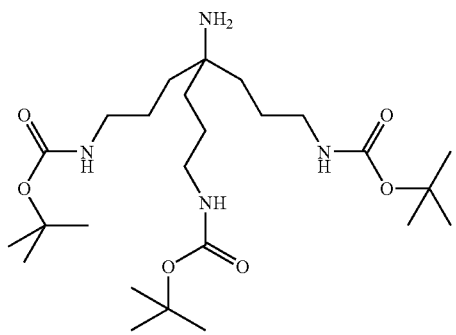

Tris(N-tert-butoxycarbonylaminoprop-3-yl)nitromethane (30 g, 59.8 mmol) prepared as described by Bradley et al, Tetrahedron, 2003, 59, 3945-3953 and Raney-nickel (30 g) in ethanol (300 ml) was hydrogenated at 30 psi at room temperature for 18 hrs. The reaction was cautiously filtered through a glass fibre filter paper avoiding sucking the catalyst dry to avoid ignition. The solution was concentrated in vacuum to afford the title compound (27.2 g, 87%) as a white foam.

$^1$H NMR (300 MHz, CDCl$_3$) δ 1.39 (bs, 39H), 3.05 (m, 6H), 4.73 (bs, 3H).

$^{13}$C NMR (75 MHz, CDCl$_3$) δ 24.1, 28.3, 37.0, 40.9, 52.7, 79.4, 155.9.

(11b) Tris(3-Tertbutoxycarboxyaminoprop-3-yl)-]phenylcarboxyamino methane

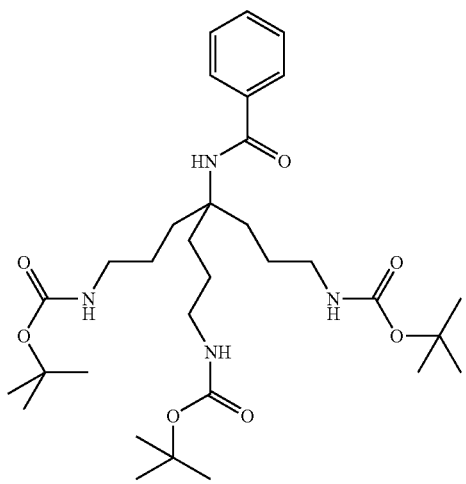

A stirred solution of (11a) (5.5 g, 11.0 mmol) in dichloromethane (100 ml) was treated with triethylamine (1.25 g, 12.4 mmol) and benzoyl chloride (1.73 g, 12.4 mmol) at room temperature for 2 hrs. The reaction was then treated with water (5 ml) and stirred for a further 0.5 hrs. The dichloromethane solution was washed with 10% aqueous potassium carbonate solution, separated, dried over sodium sulphate and concentrated in vacuum to a crisp solid (6.3 g). Chromatography on silica in a gradient of 3-10% methanol in dichloromethane gave the title compound (4.34 g, 65%) as a white solid.

$^1$H NMR (300 MHz, CDCl$_3$) δ 1.37, (bs, 33H), 1.72 (m, 6H), 3.04 (m, 6H), 4.79 (m, 3H), 5.75 (s, 1H), 7.34 (m, 3H), 7.64 (d, J=7.0 Hz, 2H).

$^{13}$C NMR (75 MHz, CDCl$_3$) δ 23.8, 28.3, 32.2, 40.6, 58.6, 79.5, 126.6, 128.4, 131.2, 135.3, 156.0, 166.9

(11c) Tris(3-aminopropyl)phenylcarboxyamino methane tris trifluoroacette salt

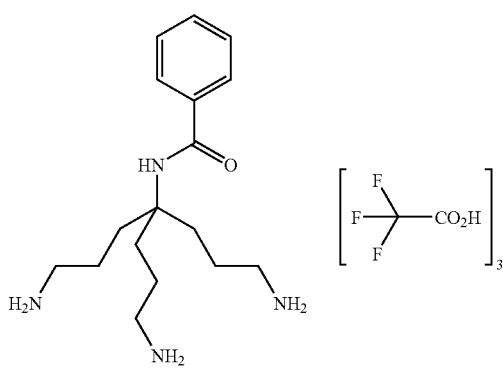

A mixture of (11b, 3 g, 4.94 mmol) in dry dichloromethane (10 ml) was treated with TFA (10 ml) at room temperature for 18 hrs. The reaction was concentrated in vacuum to a gum. Toluene (20 ml) was added and then evaporated in vacuum to a gum. This procedure was repeated three times to remove TFA. The gum was then put under high vacuum for 2 hrs to give the title compound (11c) (5.32 g, 100% yield) as a light brown solid.

$^1$H NMR (300 MHz, CD$_3$OD) δ 1.70 (m, 6H), 1.89 (m, 6H), 2.94 (m, 6H), 7.44 (m, 3H), 7.76 (m, 2H), 8.0 (bs, 1H).

$^{13}$C NMR (75 MHz, CD$_3$OD) δ 22.6, 32.6, 40.9, 59.8, 128.4, 129.5, 132.7, 136.5, 171.0

(11d) Tris((3-benzyloxy-4-oxo-4H-pyran-2-yl)carboxyaminoprop-3-yl)-]phenylcarboxy aminomethane

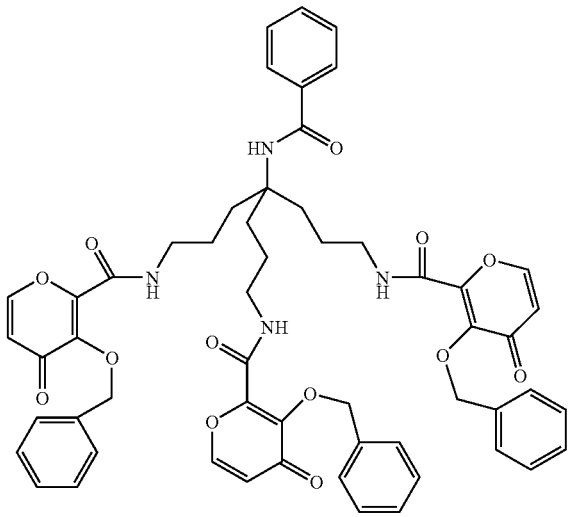

A mixture of (11c) (3.52 g, 5.4 mmol) and triethylamine (3.5 g, 34.6 mmol) in dry THF (40 ml) was treated with 2-carboxy-3-benzyloxy 1,4-dihydropyran-4-one N-hydroxy succinimide ester prepared as described in S. M. Cohen, D. T. Puerta, K, N. Raymond, J. Amer. Chem Soc 2006, 128, 2222, (5.80 g, 16.9 mmol) and stirred at room temperature for 24 hrs. Solvents were removed in vacuo, the residue partitioned between water and DCM, the aqueous layer extracted with DCM (2×30 ml), the combined organics dried over MgSO$_4$, filtered and solvents removed in vacuo to afford a gum (7 g). Chromatography on silica in a gradient of 1-10% methanol in dichloromethane gave the title compound (11d) (4.6 g, 86%). as a pale yellow solid.

$^1$H NMR (300 MHz, CDCl$_3$) δ 1.26 (m, 6H). 1.60 (m, 6H), 3.14 (m, 6H), 5.35 (s, 6H), 6.43 (d, J=5.5 Hz, 3H), 7.24-7.74 (m, 24H), 7.77 (d, J=5.8 Hz, 3H).

$^{13}$C NMR (75 MHz, CDCl$_3$) δ 24.5, 33.6, 41.4, 59.9, 77.0, 119.1, 128.2, 130.2, 130.4, 130.6 130.7, 133.2, 136.6, 136.9, 148.5, 148.6, 156.1, 160.5, 168.3, 177.3

LC/MS (Gemini C18 5µ 4.60×50 mm, 1 ml/min, 5-95% acetonitrile/0.1% formic acid in water/0.1% formic acid over 10 minutes) showed the material at 5.05 min m/z (ES$^+$) 991.3 (M$^+$H).

(11e) Tris((3-benzyloxy-1-(2-methoxyethyl)-4-oxo-4H-pyridin-2-yl)-carboxyaminoprop-3-yl)-]phenyl-carboxyaminomethane

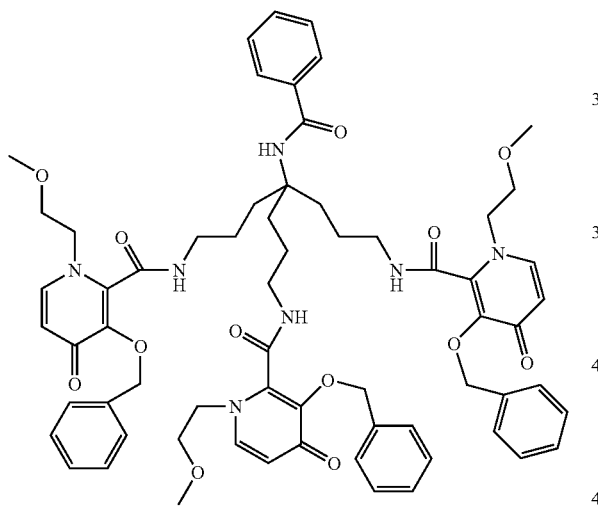

A mixture of (11e) (0.30 g, 0.3 mmol), 2-methoxyethylamine (0.18 g, 2.4 mmol) in anhydrous methanol (8 ml) under nitrogen was heated to reflux for 1 hr. The reaction mixture was concentrated in vacuo and the residue purified by column chromatography on silica, eluting with 10-30% MeOH/DCM to afford the title compound (180 mg, 52%) as a yellow solid.

$^1$H NMR (300 MHz, CDCl$_3$) δ 1.18 (m, 6H). 1.48 (m, 6H), 3.10 (m, 6H), 3.26 (s, 9H), 3.60 (m, 6H), 3.90 (m, 6H), 4.94 (s, 6H), 6.11 (d, J=7.7 Hz, 3H), 7.10-7.80 (m, 27H).

m/z (ES$^+$) 1161.5 (M$^+$H).

(11) Tris((3-hydroxy-1-(2-methoxyethyl)-4-oxo-4H-pyridin-2-yl)-carboxyaminopropyl)-phenylcarboxyaminomethane

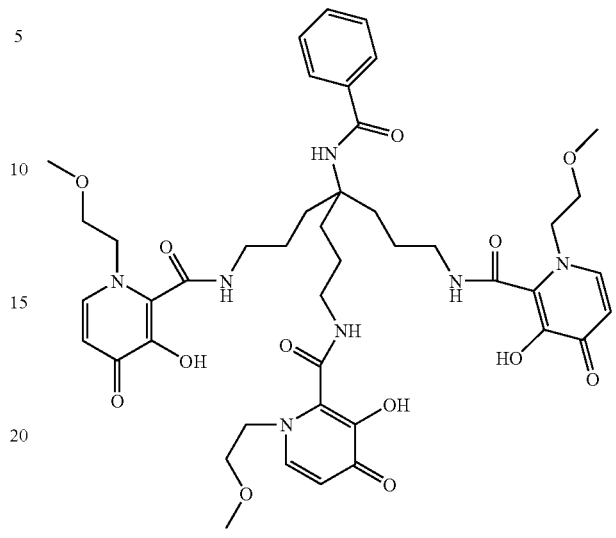

To a solution of (11e) (0.10 g, 0.09 mmol) in methanol (15 ml) was added palladium 10% wt on activated carbon (0.10 g). The mixture was hydrogenated at 2 bar at room temperature for 4 hrs. The reaction mixture was filtered twice through glass fibre filter paper and solvents removed in vacuo to afford the title compound (II) (70 mg, 87%) as an orange solid.

$^1$H NMR (300 MHz, CD$_3$OD) δ 1.68 (m, 6H). 1.98 (m, 6H), 3.31 (s, 9H), 3.40 (m, 6H), 3.61 (m, 6H), 4.31 (m, 6H), 6.31 (bs, 3H), 7.49 (m, 5H), 7.74 (bs, 3H).

$^{13}$C NMR (75 MHz, CD$_3$OD) δ 24.3, 33.6, 41.0, 56.3, 59.2, 60.3, 72.7, 111.8, 128.4, 129.5, 132.3, 137.1, 140.7, 151.4, 164.2, 170.4, 174.0 m/z (ES$^+$) 892.4 (M$^+$H).

EXAMPLE 12

Tris((3-hydroxy-1-(2-hydroxyethyl)-4-oxo-4H-pyridin-2-yl)-carboxyaminoprop-3-yl)-]phenylcarboxyaminomethane, compound of formula (I)

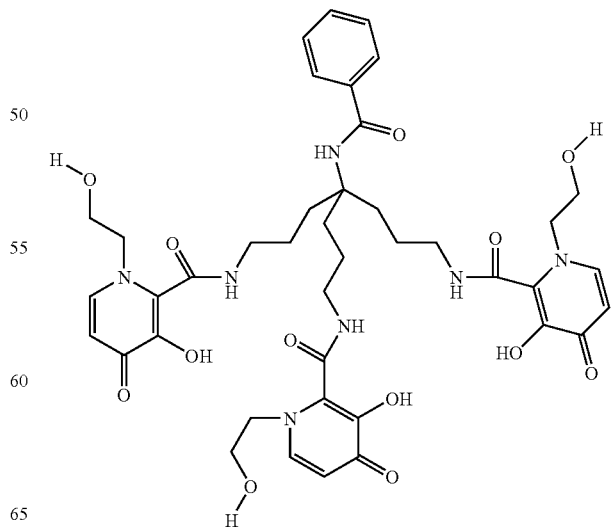

(12a) Tris((3-benzyloxy-1-(2-hydroxyethyl)-4-oxo-4H-pyridin-2-yl)-carboxyaminoprop-3-yl)-]phenyl-carboxyaminomethane

(12b) Tris((3-hydroxy-1-(2-hydroxyethyl)-4-oxo-4H-pyridin-2-yl)-carboxyaminoprop-3-yl)-]phenyl-carboxyaminomethane

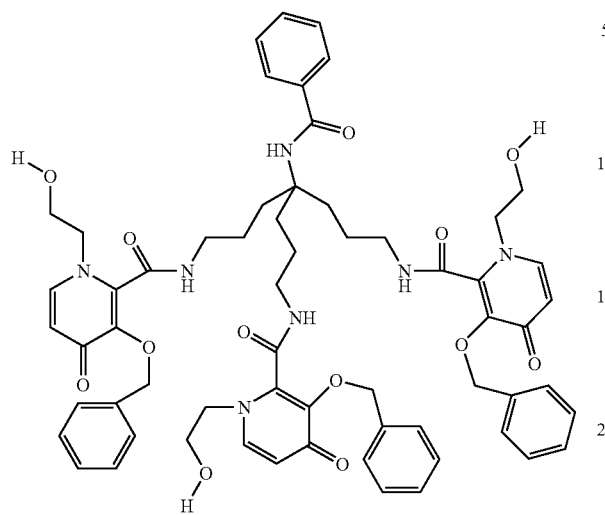
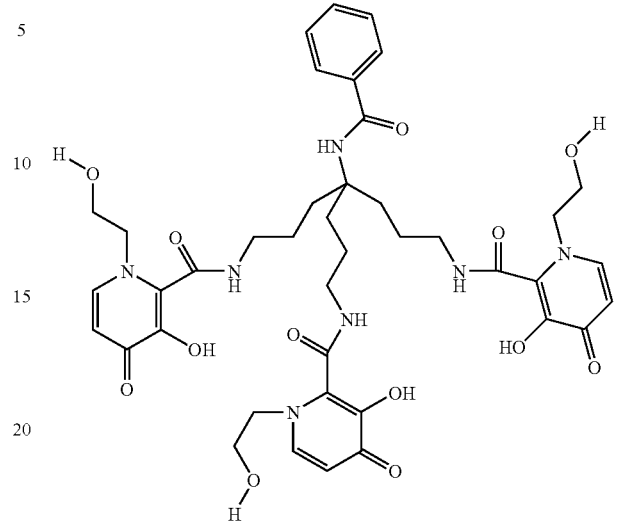

A mixture of (11d) (0.20 g, 0.2 mmol), 2-ethanolamine (98 mg, 1.6 mmol) in anhydrous methanol (5 ml) under nitrogen was heated to reflux for 1 hr. The reaction mixture was concentrated in vacuo and the residue purified by column chromatography on silica, eluting with 10-50% MeOH/DCM to afford the title compound (12a) (120 mg, 54%) as a yellow solid. The sample was azeotroped with methanol/toluene to remove final traces of 2-ethanolamine.

$^1$H NMR (300 MHz, CD$_3$OD) δ 1.30 (m, 6H). 1.64 (m, 6H), 3.20 (m, 6H), 3.81 (m, 6H), 4.01 (m, 6H), 5.05 (s, 6H), 6.45 (d, J=7.4 Hz, 3H), 7.20-7.50 (m, 18H). 7.71 (m, 5H).

$^{13}$C NMR (75 MHz, CD$_3$OD) δ24.0, 33.4, 41.1, 58.0, 59.8, 61.9, 75.6, 118.5, 128.3, 129.3, 129.4, 129.5, 129.6, 129.7, 132.5, 136.8, 138.3, 142.1, 142.2, 146.2, 162.7, 170.2, 175.7 m/z (ES$^+$) 1120.5 (M+H).

To a solution of (12a) (0.10 g, 0.09 mmol) in methanol (15 ml) was added palladium 10% wt on activated carbon (0.10 g). The mixture was hydrogenated at 2 bar at room temperature for 4 hrs. The reaction mixture was filtered twice through glass fibre filter paper and solvents removed in vacuo to afford the title compound (12b) (58 mg, 68%) as an orange solid.

$^1$H NMR (300 MHz, D$_2$O) δ 1.64 (m, 6H). 1.89 (m, 6H), 3.40 (m, 6H), 3.75 (m, 6H), 4.12 (m, 6H), 6.44 (bs, 3H), 7.20-7.90 (m, 8H).

m/z (ES$^+$) 850.3 (M$^+$H).

EXAMPLE 13

Tris((3-hydroxy-1-(2,3,4,5,6-pentahydroxyhexyl)-4-oxo-4H-pyridin-2-yl)-carboxyaminoprop-3-yl)-]phenylcarboxyaminomethane gadolinium (III) salt, compound of formula (II)

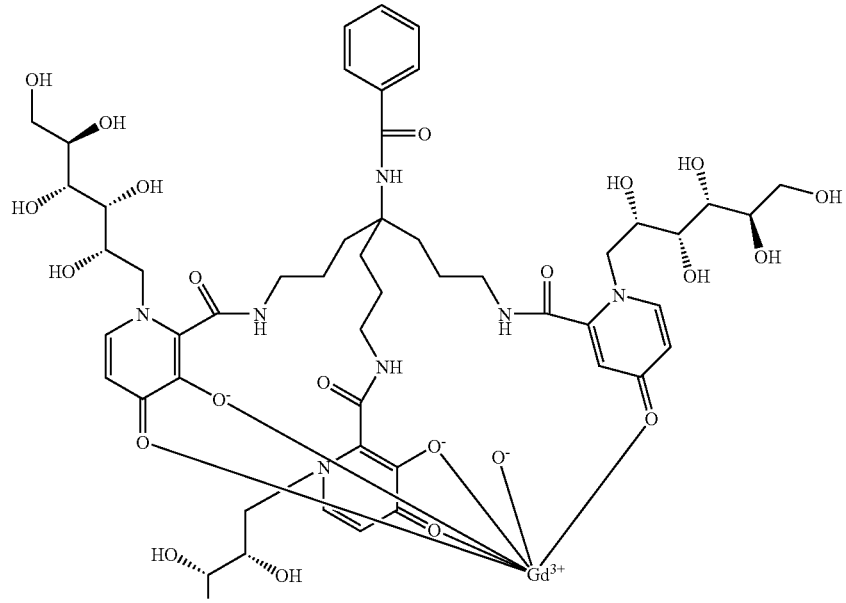

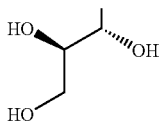

(13a) Tris((3-benzyloxy-1-(2,3,4,5,6-pentahydroxy-hexyl)-4-oxo-4H-pyridin-2-yl)-carboxyaminoprop-3-yl)-]phenylcarboxyaminomethane

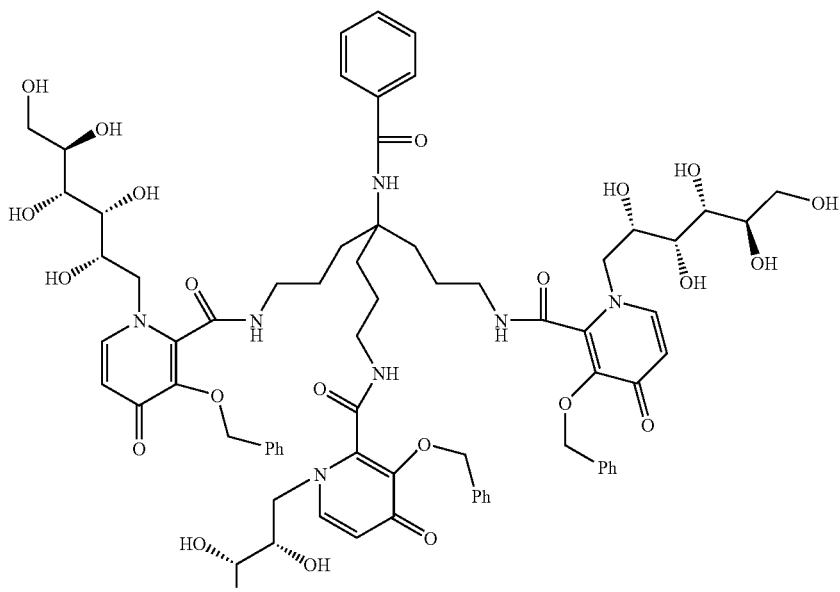

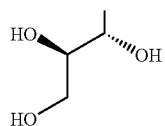

A mixture of (11d) Tris((3-benzyloxy-4-oxo-4H-pyran-2-yl)-carboxyaminoprop-3-yl)-phenylcarboxy aminomethane (2.95 g, 3.0 mmol), D-glucamine (3.3 g, 18.2 mmol) in anhydrous methanol (90 ml) under nitrogen was heated to reflux for 4 hrs. LCMS indicated that heating for more than 4 hrs led to decomposition. The reaction mixture was concentrated in vacuo and the residue purified by column chromatography on reverse phase silica, eluting with 10-40% MeOH/H$_2$O to give impure compound (4 g). The purification was repeated to afford the title compound (13a) (700 mg, 16%) as yellow crystals.

$^1$H NMR (300 MHz, DMSO) δ 1.30-1.45 (m, 6H). 1.55-1.70 (m, 6H), 3.00-3.20 (m, 6H), 3.30-4.10 (m, 24H), 4.30-4.45 (m, 6H), 4.50-4.65 (m, 6H), 4.90-5.20 (m, 9H), 6.22 (d, J=7.7 Hz, 3H), 7.15-7.80 (m, 24H), 8.75 (bt, 3H, NH).

$^{13}$C NMR (75 MHz, DMSO) δ 22.8, 32.1. 39.5, 56.4, 58.0, 63.3, 69.6, 71.3, 71.4, 72.4, 72.7, 116.6, 127.4, 127.8, 127.9, 128.1, 128.2, 130.8, 135.9, 137.7, 139.8, 140.6, 144.1, 160.6, 166.8, 172.8

LC/MS (Gemini C18 5μ 4.60×50 mm, 1 ml/min, 5-95% acetonitrile/0.1% formic acid in water/0.1% formic acid over 10 minutes) showed the material at 4.04 min m/z (ES$^+$) 1480.6 (M$^+$H).

(13b) Tris((3-hydroxy-1-(2,3,4,5,6-pentahydroxy-hexyl)-4-oxo-4H-pyridin-2-yl)-carboxyaminoprop-3-yl)phenylcarboxyaminomethane

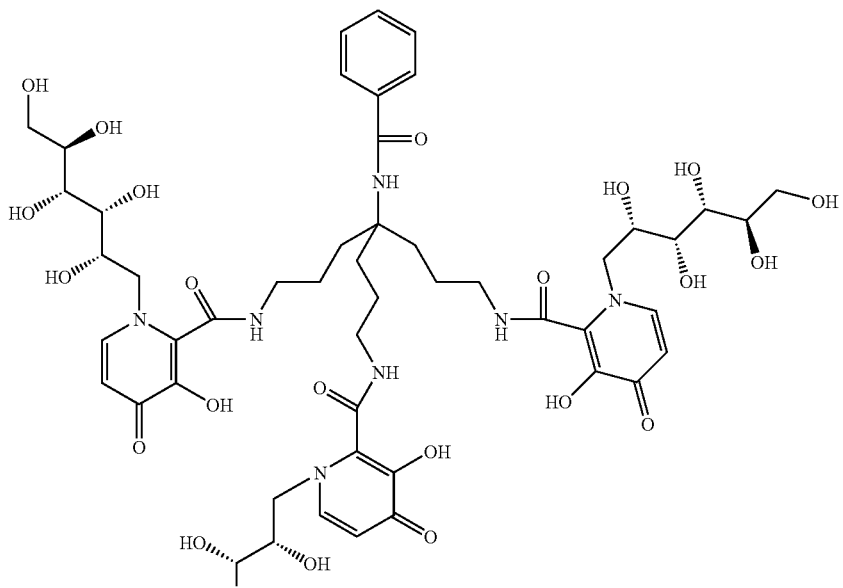

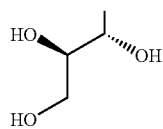

To a solution of (13a, 0.66 g, 0.45 mmol) in water (12 ml) and methanol (12 ml) was added palladium 10% wt on activated carbon (0.25 g). The mixture was hydrogenated at 2 bar at room temperature for 18 hrs. The reaction mixture was filtered through glass fibre filter paper, the paper washed with water (10 ml), methanol from the filtrate removed in vacuo and freezed-dried to afford the title compound (450 mg, 83%) as a light brown solid.

Note: all glassware and reaction vessels were soaked with 5 N HCl, washed with distilled water and dried in an oven to remove any potential iron contamination.

$^1$H NMR (300 MHz, D$_2$O) δ 1.50-1.70 (m, 6H). 1.75-2.00 (m, 6H), 3.30-3.50 (m, 6H), 3.50-4.40 (m, 24H), 6.42 (d, J=6.4 Hz, 3H), 7.30-7.70 (m, 8H).

$^{13}$C NMR (75 MHz, D$_2$O) δ22.4, 32.0, 40.3, 57.8, 59.5, 62.8, 70.3, 71.1, 71.3, 72.0, 113.0 127.2, 128.8, 129.4, 132.0, 135.0, 140.5, 146.1, 162.5, 170.9, 171.4.

LC/MS (Gemini C18 5µ 4.60×50 mm, 1 ml/min, 5-95% acetonitrile/0.1% formic acid in water/0.1% formic acid over 10 minutes) showed the material at 2.02 min m/z (ES$^+$) 1210.6 (M$^+$H).

Elemental analysis: % calculated C, 49.65; H, 6.52; N, 7.65. % found C, 49.48; H, 6.26; N, 7.76. The experimental values are consistent with the presence of four water molecules, giving the new molecular formula of C$_{53}$H$_{83}$N$_7$O$_{29}$

(13) Tris((3-hydroxy-1-(2,3,4,5,6-pentahydroxy-hexyl)-4-oxo-4H-pyridin-2-yl)-carboxyaminoprop-3-yl)-]phenylcarboxyaminomethane gadolinium (III) salt

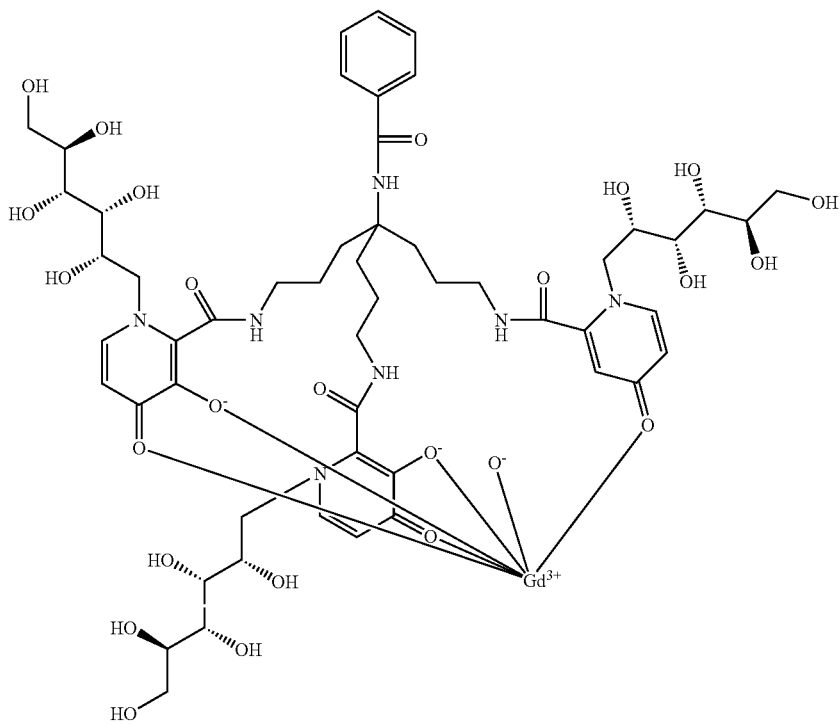

To a solution of (13b) (300 mg, 0.234 mmol) in water (4 ml) was added gadolinium acetate (62.5 mg, 0.187 mmol). The reaction mixture was heated at 40° C. for 72 hrs, cooled and solvents removed in vacuo to give the title compound (13) (316 mg, 99%) as a pale brown solid.

LC-MS and EA indicated approximately a 1:1 mixture of chelate and chelant. The xylenol orange sodium salt test indicated no presence of free $Gd^{3+}$.

LC/MS (Gemini C18 5μ 4.60×50 mm, 1 ml/min, 3-20% acetonitrile in water over 12 minutes) showed the product at 4.86 min m/z ($ES^+$) 1364.7 ($M^+H$) and starting material at 6.48 min m/z ($ES^+$) 1210.6 ($M^+H$).

Elemental analysis: % calculated C, 46.66; H, 5.32; N, 7.18; Gd, 11.52. found C, 46.31; H, 5.71; N, 6.58; Gd, 6.65.

EXAMPLE 14

Tris((3-hydroxy-1-(2,3-dihydroxypropyl)-4-oxo-4H-pyridin-2-yl)-carboxyamino prop-3-yl)-phenylcarboxyaminomethane, compound of formula (I)

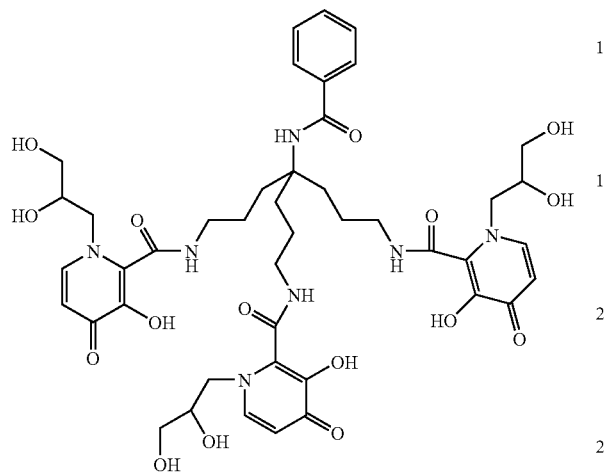

(14a) Tris((3-benzyloxy-1-(2,3-dihydroxypropyl)-4-oxo-4H-pyridin-2-yl)-carboxyaminoprop-3yl)-)phenylcarboxyaminomethane

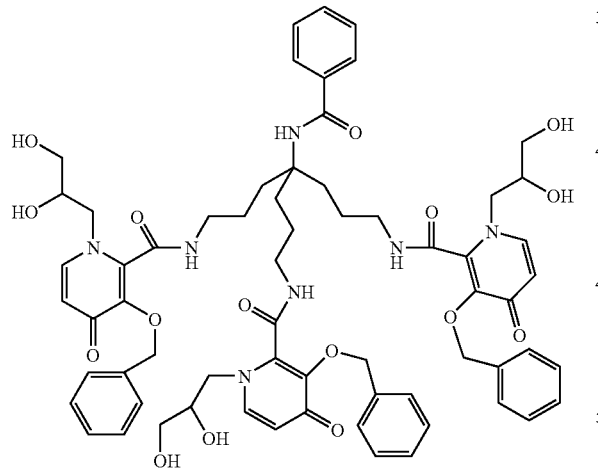

A mixture of (11d) Tris((3-benzyloxy-4-oxo-4H-pyran-2-yl)carboxyaminoprop-3-yl)-]phenylcarboxy aminomethane (2.6 g, 2.6 mmol), 3-amino-1,2-propanediol (1.4 g, 15.6 mmol) in anhydrous methanol (25 ml) under nitrogen was heated to reflux for 2 hrs. The reaction mixture was concentrated in vacuo and the residue purified by column chromatography on reverse phase silica, eluting with 60-80% MeOH/H$_2$O to give impure compound (0.9 g). The purification was repeated to afford the title compound (14a) (740 mg, 24%) as a yellow solid.

$^1$H NMR (300 MHz, CD$_3$OD) δ 1.10-1.45 (m, 6H). 1.55-1.70 (m, 6H), 3.10-3.30 (m, 6H), 3.40-3.60 (m, 6H), 3.75-4.00 (m, 6H), 4.10-4.25 (m, 3H), 4.95-5.15 (m, 6H), 6.45 (d, J=7.3 Hz, 3H), 7.15-7.55 (m, 18H), 7.71 (m, 5H).

$^{13}$C NMR (75 MHz, CD$_3$OD) δ24.0, 33.3, 41.1, 58.7, 59.9, 64.8, 72.2, 75.6, 75.7, 118.4, 128.4, 129.35, 129.41, 129.5, 129.56, 129.63, 129.7, 129.8, 132.5, 136.8, 138.30, 138.35, 142.1, 142.2, 142.6, 146.17, 146.20, 146.25, 162.7, 170.2, 175.7, 175.8

LC/MS (Gemini C18 5µ 4.60×50 mm, 1 ml/min, 5-95% acetonitrile/0.1% formic acid in water/0.1% formic acid over 10 minutes) showed the material at 4.48 min m/z (ES$^+$) 1210.7 (M$^+$H).

Note: Product chromatographed mainly as a mixture of two peaks (diastereoisomers) which give the same M$^+$H.

(14b) Tris((3-hydroxy-1-(2,3-dihydroxypropyl)-4-oxo-4H-pyridin-2-yl)-carboxyaminoprop-3-yl)-] phenylcarboxyaminomethane

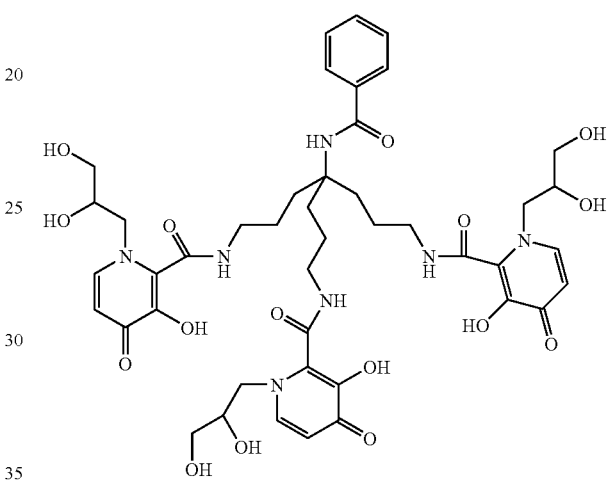

To a solution of (14a) Tris((3-benzyloxy-1-(2,3-dihydroxypropyl)-4-oxo-4H-pyridin-2-yl)-carboxyaminoprop-3yl)-) phenylcarboxyaminomethane (0.74 g, 0.61 mmol) in water (10 ml) and methanol (30 ml) was added palladium 10% wt on activated carbon (0.40 g). The mixture was hydrogenated at 2 bar at room temperature for 6 hrs. The reaction mixture was filtered through glass fibre filter paper, the paper washed with water (10 ml), methanol from the filtrate removed in vacuo and freezed-dried to afford the title compound (540 mg, 94%) as a light brown solid.

Note: all glassware and reaction vessels were soaked with 5 N HCl, washed with distilled water and dried in an oven to remove any potential iron contamination.

$^1$H NMR (300 MHz, D$_2$O) δ 1.50-1.75 (m, 6H). 1.80-2.00 (m, 6H), 3.30-3.55 (m, 12H), 3.75-4.00 (m, 6H), 4.15-4.30 (m, 3H), 6.44 (d, J=7.1 Hz, 3H), 7.35-7.70 (m, 8H).

$^{13}$C NMR (75 MHz, D$_2$O) δ22.5, 32.0, 40.3, 57.7, 59.5, 63.0, 71.0, 113.0, 127.2, 128.8, 129.5, 132.0, 135.1, 140.4, 146.0, 162.5, 170.8, 171.4

LC/MS (Gemini C18 5µ 4.60×50 mm, 1 ml/min, 5-95% acetonitrile/0.1% formic acid in water/0.1% formic acid over 6 minutes) showed the material at 2.00 min m/z (ES$^+$) 940.4 (M$^+$H).

EXAMPLE 15

Measurement of Longitudinal Relaxivity $T_1$ was measured by the inversion recovery method as described by Timothy D. W. Claridge, in "High-Resolution NMR Techniques in Organic Chemistry" Pergamon Amsterdam 1999, 26-30.

| Example | r1 at 10 MHz s-1 mM | r1 at 20 MHz s-1 mM | r1 at 60 MHz s-1 mM |
|---|---|---|---|
| 1 | 9.7 | 11.6 | 9.5 |

EXAMPLE 16

Measurement of the Stability of Gadolinium Chelates

Stabilities of the gadolinium complexes of the chelates were measured by a spectrophotometric method using the principle that there is a change in UV absorbance of these compounds as the hydroxyl group on the pyridinone ring deprotonates. There is a significant decrease in the wavelength of the UV maximum as the proton is removed. The UV absorbance of the chelants at different pH's was determined to measure the UV absorbance at different degrees of protonation. The measurements were then repeated in the presence of 1 equivalent of gadolinium (III) and the effect on the UV absorbtion as a function of pH measured. A software program was used to analyze the data and calculate the affinity of the chelates for gadolinium.

TABLE 1

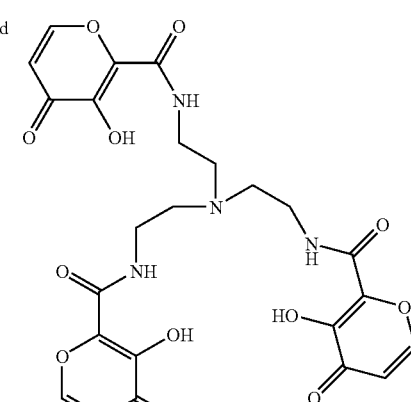

| Example number | CHELANT STRUCTURE | Gd Chelate STABILITY CONSTANT (LogK$_{GdL}$) |
|---|---|---|
| Standard | 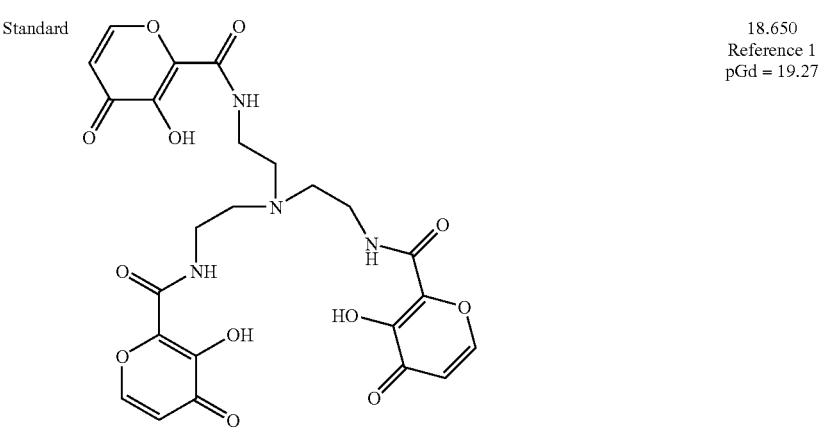 | 18.650 Reference 1 pGd = 19.27 |
| 4 | 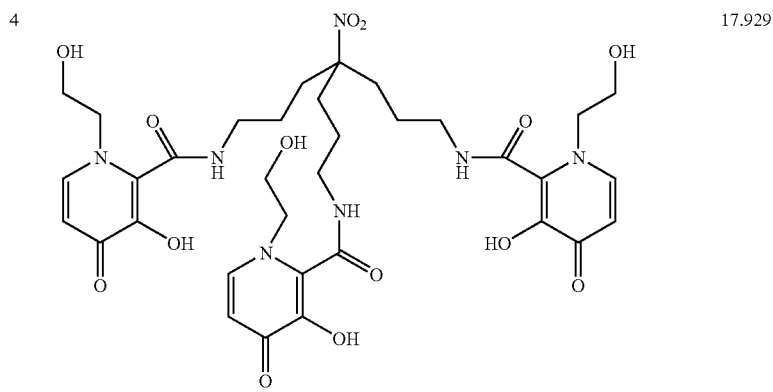 | 17.929 |

TABLE 1-continued of stabilities of gadolinium (III) complexes

| Example number | CHELANT STRUCTURE | Gd Chelate STABILITY CONSTANT (LogK$_{GdL}$) |
|---|---|---|
| 11 | | 15.716 |
| 12 | | 18.284 |
| 3 | | 21.287 |

EXAMPLE 17

The solubility of the gadolinium chelates in table 2 was measured by HPLC analysis of the concentrations of compound in aqueous solutions at 20° C. after equilibration by shaking for a few hours. Increasing amounts of compound were added to a measured volume of water until addition of further amounts did not increase the concentration of compound in solution. This indicated the saturation point of the solution.

TABLE 2

Solubility of gadolinium (III) chelates

| Example Number | R | Water solubility of chelate |
|---|---|---|
| 1e | —CH$_2$CH$_2$OCH$_3$ | <0.5 mg/ml |
| 4 | —CH$_2$CH$_2$OH | <0.5 mg/ml |
| 5 | —CH$_2$C(CH$_3$)$_2$CH$_2$OCH$_2$CH$_2$OH | <1 mg/ml |
| 6 | —CH$_2$CH(OH)CH$_2$OH (branched) | 3.4 mg/ml |
| 7 | triol substituent | ~10 mg/ml* <br> *Kinetic solubility, but some compound precipitates on standing |
| 8 | pentol substituent | >200 mg/ml |

What is claimed is:

1. A compoud of general formula (I)

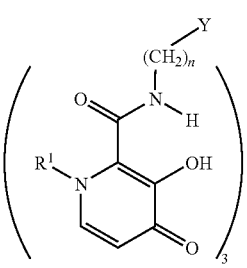

wherein
R$^1$ is C$_{2-6}$ alkyl substituted with OH or O—C$_{1-3}$ alkyl; or polyethylene glycol of up to 3 monomer units;
n is 1-4; and
Y is a group of the formula:

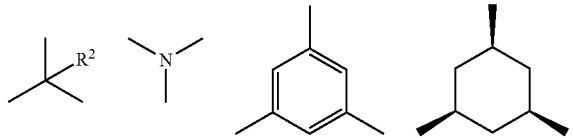

wherein:
R$^2$ is H, (CH$_2$)$_m$NH$_2$, (CH$_2$)$_m$NHCOPh, (CH$_2$)$_m$NH-COCH$_3$, (CH$_2$)$_m$CO$_2$H or (CH$_2$)$_m$NO$_2$;
m is 0-3; and
Ph is phenyl.

2. A compound according to claim 1, wherein R$^1$ is C$_{2-6}$ alkyl substituted with —O—C$_{1-3}$ alkyl.

3. A compound according to claim 2, wherein R$^1$ is C$_{2-4}$ alkyl substituted with methoxy or ethoxy.

4. A compound according to claim 3, wherein R$^1$ is methoxyethyl.

5. A compound according to claim 1, wherein Y is a group of the formula:

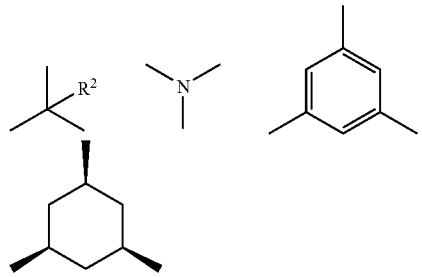

wherein:
R$^2$ is H, (CH$_2$)$_m$NH$_2$, (CH$_2$)$_m$NHCOPh, (CH$_2$)$_m$NH-COCH$_3$, (CH$_2$)$_m$CO$_2$H or (CH$_2$)$_m$NO$_2$;
m is 0-3; and
Ph is phenyl.

6. A compound according to claim 1 attached to a peptide, protein, polymer or dendrimer via the trivalent group Y.

7. A process for the preparation of a compound of general formula (I)

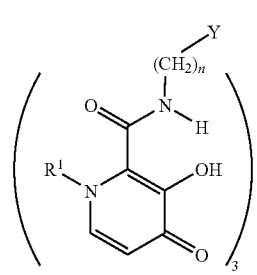

(I)

wherein
R$^1$ is C$_{2-6}$ alkyl substituted with OH or O—C$_{1-3}$ alkyl; or polyethylene glycol of up to 3 monomer units;
n is 1-4; and
Y is a group of the formula:

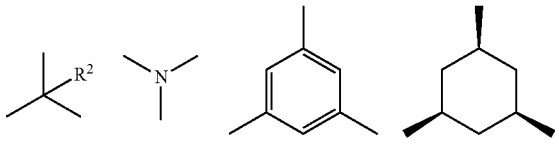

wherein:
R$^2$ is H, (CH$_2$)$_m$NH$_2$, (CH$_2$)$_m$NHCOPh, (CH$_2$)$_m$NH-COCH$_3$, (CH$_2$)$_m$CO$_2$H or (CH$_2$)$_m$NO$_2$;
m is 0-3; and
Ph is phenyl,
comprising the steps of:
reacting a protected compound of general formula (III)

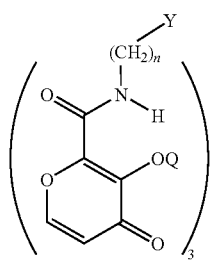

(III)

wherein:
n is 1-4; and
Y is a group of the formula:

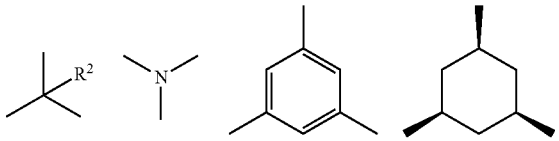

wherein:
R$^2$ is H, (CH$_2$)$_m$NH$_2$, (CH$_2$)$_m$NHCOPh, (CH$_2$)$_m$NH-COCH$_3$, (CH$_2$)$_m$CO$_2$H or (CH$_2$)$_m$NO$_2$;
m is 0-3; and
Ph is phenyl; and
Q is a protecting group;
with a compound of general formula (IV):

$$R^1\text{—}NH_2 \qquad (IV)$$

wherein R$^1$ is C$_{2-6}$ alkyl substituted with OH or O—C$_{1-3}$ alkyl; or polyethylene glycol of up to 3 monomer units;
to give a protected compound of general formula (V):

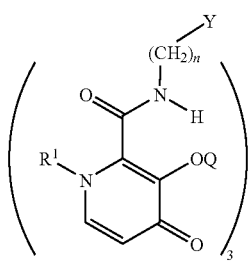

(V)

wherein R¹, n, Y and Q are each as set forth above; and removing the protecting group Q.

8. A compound of general formula (II):

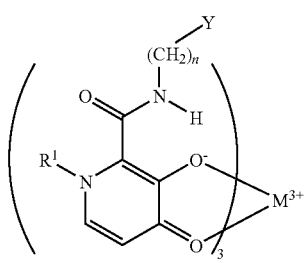

(II)

wherein

R¹ is $C_{2-6}$ alkyl substituted with OH or O—$C_{1-3}$ alkyl; or polyethylene glycol of up to 3 monomer units;

n is 1-4;

Y is a group of the formula:

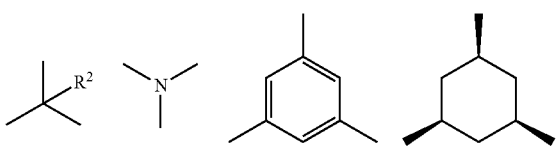

wherein:

R² is H, $(CH_2)_m NH_2$, $(CH_2)_m NHCOPh$, $(CH_2)_m NH\text{-}COCH_3$, $(CH_2)_m CO_2H$ or $(CH_2)_m NO_2$;

m is 0-3; and

Ph is phenyl; and

M is a paramagnetic metal ion.

9. A compound according to claim 8, wherein M is a paramagnetic metal ion of atomic numbers 25, 26, 57 or 60 to 68.

10. A compound according to claim 9, wherein M is a paramagnetic metal ion of Mn, Fe, La, Eu, Gd or Dy.

11. A compound according to claim 10, wherein M is Gd.

12. A compound according to claim 8, wherein R¹ is $C_{2-6}$ alkyl substituted with —O—$C_{1-3}$ alkyl.

13. A compound according to claim 12, wherein R¹ is $C_{2-4}$ alkyl substituted with methoxy or ethoxy.

14. A compound according to claim 13, wherein R¹ is methoxyethyl.

15. A compound according to claim 8, wherein Y is a group of the formula:

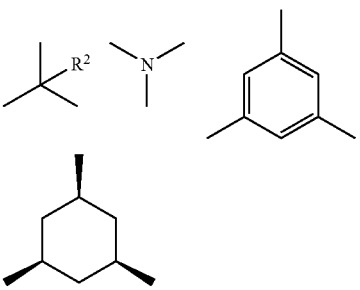

wherein:

R² is H, $(CH_2)_m NH_2$, $(CH_2)_m NHCOPh$, $(CH_2)_m NH\text{-}COCH_3$, $(CH_2)_m CO_2H$ or $(CH_2)_m NO_2$;

m is 0-3; and

Ph is phenyl.

16. A compound according to claim 8 attached to a peptide, protein, polymer or dendrimer via the trivalent group Y.

17. A process for the preparation of a compound of general formula (II):

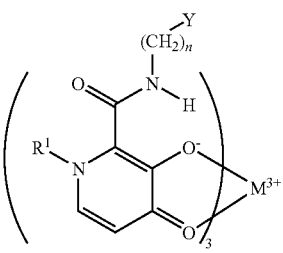

(II)

wherein

R¹ is $C_{2-6}$ alkyl substituted with OH or O—$C_{1-3}$ alkyl; or polyethylene glycol of up to 3 monomer units;

n is 1-4;

Y is a group of the formula:

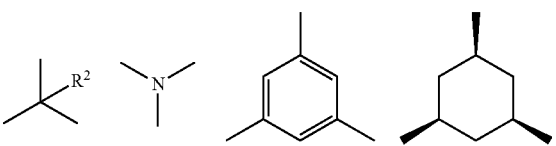

wherein:

R² is H, $(CH_2)_m NH_2$, $(CH_2)_m NHCOPh$, $(CH_2)_m NH\text{-}COCH_3$, $(CH_2)_m CO_2H$ or $(CH_2)_m NO_2$;

m is 0-3; and

Ph is phenyl; and

M is a paramagnetic metal ion, comprising the step of reacting a protected compound of general formula (I) of general formula (I)

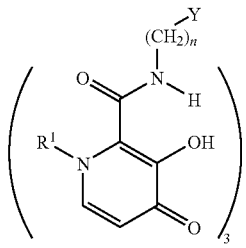
(I)

wherein $R^1$ is $C_{2-6}$ alkyl substituted with OH or O—$C_{1-3}$ alkyl; or polyethylene glycol of up to 3 monomer units;

n is 1-4; and

Y is a group of the formula:

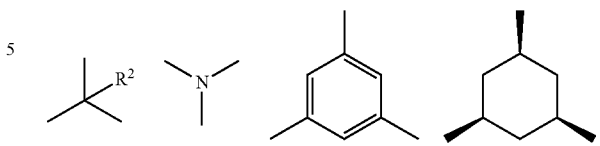

wherein:

$R^2$ is H, $(CH_2)_m NH_2$, $(CH_2)_m NHCOPh$, $(CH_2)_m NHCOCH_3$, $(CH_2)_m CO_2 H$ or $(CH_2)_m NO_2$;

m is 0-3; and

Ph is phenyl with a water soluble salt of said paramagnetic metal ion M.

18. A process according to claim 17, wherein said water soluble salt of said paramagnetic metal ion M is a nitrate.

* * * * *